(12) United States Patent
Borsi et al.

(10) Patent No.: US 8,491,906 B2
(45) Date of Patent: Jul. 23, 2013

(54) SELECTIVE TARGETING OF TUMOR VASCULATURE USING ANTIBODY MOLECULES

(75) Inventors: Laura Borsi, Genoa (IT); Barbara Carnemolla, Genoa (IT); Enrica Balza, Genoa (IT); Patrizia Castellani, Genoa (IT); Luciano Zardi, Genoa (IT); Matthias Friebe, Berlin (DE); Christoph-Stephan Hilger, Berlin (DE)

(73) Assignees: Philogen S.p.A., Sienna (IT); Bayer Schering Pharma AG, Berlin (DE)

( * ) Notice: Subject to any disclaimer, the term of this patent is extended or adjusted under 35 U.S.C. 154(b) by 1995 days.

(21) Appl. No.: 10/507,178

(22) PCT Filed: Mar. 11, 2003

(86) PCT No.: PCT/IB03/01458
§ 371 (c)(1),
(2), (4) Date: May 31, 2005

(87) PCT Pub. No.: WO03/076469
PCT Pub. Date: Sep. 18, 2003

(65) Prior Publication Data
US 2006/0057146 A1 Mar. 16, 2006

Related U.S. Application Data

(60) Provisional application No. 60/363,045, filed on Mar. 11, 2002.

(51) Int. Cl.
*A61K 39/395* (2006.01)
*C07K 16/30* (2006.01)

(52) U.S. Cl.
USPC .................................. 424/155.1; 530/388.8

(58) Field of Classification Search
USPC .................................. 424/155.1; 530/388.8
See application file for complete search history.

(56) References Cited

U.S. PATENT DOCUMENTS 7,273,924 B1 9/2007 Neri et al.
2009/0214423 A1* 8/2009 Borsi et al. ................... 424/1.49

FOREIGN PATENT DOCUMENTS

| EP | 1 130 099 | 9/2001 |
| WO | WO 94 09817 | 5/1994 |
| WO | WO 99 58570 | 11/1999 |
| WO | WO 01 62800 | 8/2001 |
| WO | WO 03 055917 | 7/2003 |

OTHER PUBLICATIONS

Viti et al. (Can. Res. 59:347-352 (1999)).*
Rudikoff et al (Proc Natl Acad Sci, 1982. vol. 79, p. 1979).*
MacCallum et al. (J. Mol. Biol., 1996. vol. 262, pp. 732-745).*
de Pascalis et al. (The Journal of Immunology, 2002. vol. 169, pp. 3076-3084).*
Casset et al. (BBRC, 2003. vol. 307, pp. 198-205).*
Vajdos et al. (J. Mol. Biol., 2002. vol. 320, pp. 415-428).*
Orlova, et al. (Cancer Biotherapy and Radiopharmaceuticals, 2002. vol. 17 No. 4, pp. 385-396).*
Pini et al. (J Biol Chem, 273: 21769-21776, 1998).*
Viti et al., (Cancer Res, 59: 347-353, 1999).*
Tarli et al., (Blood, 94:192-198, 1999).*
Batista et al. (J. Exp. Med., 184: 2197-2206, 1996).*
Carnemolla et al, Blood, Mar. 1, 2002, vol. 99, No. 5, pp. 1659-1665.
Wu et al, Proc. Natl. Acad. Sci. USA, Jul. 18, 2000, vol. 97, No. 15, pp. 8495-8500.
Lui et al, Blood, Sep. 15, 1998, vol. 92, No. 6, pp. 2103-2112.
Vangelista et al, Protein Engineering, Jan. 2002, vol. 15, No. 1, pp. 51-57.
Bestagno et al, Biochemistry, Sep. 4, 2001, vol. 40, No. 35, pp. 10686-10692.
U.S. Appl. No. 10/321,558, filed Dec. 18, 2002 and published Sep. 18, 2003 under Publication No. US-2003-0176663-A1.
U.S. Appl. No. 11/637,810, filed Dec. 13, 2006 and published Aug. 16, 2007 under Publication No. US-2007-0189963-A1.
U.S. Appl. No. 10/821,930, filed Apr. 12, 2004 and published on Jun. 22, 2006 under Publication No. US-2006-0133994-A1.
U.S. Appl. No. 10/937,882, filed Sep. 10, 2004 and published on Apr. 7, 2005 under Publication No. US-2005-0074401-A1.
U.S. Appl. No. 10/204,581, filed Mar. 10, 2003 and published on Jan. 22, 2004 under Publication No. US 2004-0013640 A1.
U.S. Appl. No. 11/105,475, filed Apr. 14, 2005 and published on Oct. 6, 2005 under Publication No. US-2005-0221434-A1.
U.S. Appl. No. 10/336,041, filed Jan. 3, 2003 and published on Jan. 1, 2004 under Publication No. US-2004-0001790-A1.
U.S. Appl. No. 10/088,866, filed Jul. 2, 2002.
U.S. Appl. No. 10/966,097, filed Oct. 18, 2004 and published on May 26, 2005 under Publication No. US-2005-0112690-A1.
U.S. Appl. No. 11/249,296, filed Oct. 14, 2005 and published on Jun. 1, 2006 under Publication No. US-2006-0115428-A1.
Li Erqui et al.: "Mammalian cell expression of dimeric small immune proteins (SIP)"; Protein Engineering, vol. 10, No. 6, pp. 731-736, (1997).
Batista F D et al.; "The two membrane isoforms of human IgE assemble into functionally distinct B cell Antigen receptors"; The Journal of Experimental Medicine., Dec. 1, 1996, vol. 184, No. 6, pp. 2197-2205.
Pini A et al.: "Design and use of a phage display library. Human Antibodies with sunanomolar affinit against a marker of angiogenesis eluted from a two-dimensional gel" Journal of Biological Chemistry, American Society of Biological Chemists, Baltimore, MD, UJS vol. 273, No. 34, Aug. 21, 1998, pp. 21769-21776.
Borsi Laura et al.: "Selective targeting of tumoral vasculature: comparsion of different formats of an antibody (L19)to the ED-B domain of fibronectin." International Journal of Cancer Journal International Du Cancer, United States, Nov. 1, 2002, vol. 102, No. 1, pp. 75-85.

* cited by examiner

*Primary Examiner* — Lynn Bristol
(74) *Attorney, Agent, or Firm* — Millen, White, Zelano & Branigan, P.C.

(57) ABSTRACT

The present invention relates to selectively targeting tumoral vasculature in vivo using a human recombinant scFv, L19, to the angiogenesis marker ED-B domain of fibronectin. In preferred embodiments, a complete human IgG1 is employed having the variable regions of L19. In other preferred embodiments is employed a mini-immunoglobulin generated by fusing the scFv L19 to the constant CH4 domain of a secretory IgE isoform that naturally contains a cysteine in its COOH terminal and which forms a covalently linked dimer. Different in vivo behavior of the antibody formats is exploitable for different diagnostic and/or therapeutic purposes, depending on clinical needs and disease. The antibody molecules may be labelled as described.

13 Claims, 5 Drawing Sheets

L19scFv/pDN322

L19SIP/pCDNA3

L19HIgG1/pcDNA3

L19kL/pCMV2Δ

SELECTIVE TARGETING OF TUMOR VASCULATURE USING ANTIBODY MOLECULES

SEQUENCE LISTING

The instant application contains a Sequence Listing which has been submitted in ASCII format via EFS-Web and is hereby incorporated by reference in its entirety. Said ASCII copy, created on Oct. 3, 2011, is named PHIL0001.txt and is 2,914 bytes in size.

The present invention relates to targeting of tumor vasculature using antibody molecules. In particular, the invention relates to use of antibody molecules that bind ED-B of fibronectin, and which are of demonstrated usefulness in tumor targeting. In different embodiments of the present invention, antibody molecules are employed in different molecular formats. In certain embodiments the antibody molecules comprise human IgG1. In other embodiments the antibody molecules are mini-immunoglobulins, such as are generated by fusing an scFv antibody molecule to the constant CH4 domain of a secretory IgE isoform that naturally contains a cysteine in its COOH terminal which forms a covalently linked dimer. Blood clearance rate, in vivo stability and other advantageous properties are employed in different aspects and embodiments of the invention, e.g. in tumor targeting. The different in vivo behavior of different antibody molecule formats may be exploited for different diagnostic and/or therapeutic purposes, depending on clinical needs and disease.

Despite their enormous potential as therapeutic agents, monoclonal antibodies (mAbs) of non-human origin have performed poorly in clinical trials as a result of their immunogenicity (1 Shawler et al., 1985; 2 Miller et al., 1983), poor pharmacokinetic properties (3 Hakimi et al., 1991; 4 Stephens et al., 1995) and inefficiency in recruiting effector functions (5 Riechmann et al., 1988; 6 Junghens et al., 1990). The recent prospect of isolating human antibody fragments from phage display libraries (7 McCafferty et al., 1990; 8 Lowman et al., 1991; for reviews see 9 Nilsonn et al., 2000 and 10 Winter et al., 1994) transcends these problems, revitalizing studies and rekindling hopes of using these reagents to treat major diseases. Indeed, these molecules should serve as ideal building blocks for novel diagnostic and therapeutic tools (11 Reichert, 2001; 12 Huls et al., 1999). Furthermore, these antibodies can be "matured" to reach affinities in the picomolar range (13 Pini et al., 1998), at least desirable, if not necessary, for their clinical use.

Clinical applications of human antibody fragments for the selective delivery of diagnostic or therapeutic agents nonetheless require highly specific targets. In the case of tumors, the most popular targets are cell-surface antigens, which are usually neither abundant nor stable. Nevertheless, during tumor progression, the microenvironment surrounding tumor cells undergoes extensive modification that generates a "tumoral environment" which represents a target for antibody-based tumor therapy (14 Neri and Zardi, 1998). In fact, the concept that the altered tumor microenvironment is itself a carcinogen that can be targeted is increasingly gaining consensus. Molecules that are able to effectively deliver therapeutic agents to the tumor microenvironment thus represent promising and important new tools for cancer therapy (15 Bissel, 2001; 14 Neri and Zardi, 1998).

Fibronectin is an extracellular matrix (ECM) component that is widely expressed in a variety of normal tissues and body fluids. Different FN isoforms can be generated by the alternative splicing of the FN pre-mRNA, a process that is modulated by cytokines and extracellular pH (16 Balza et al., 1988; 17 Carnemolla et al., 1989; 18 Borsi et al., 1990; 19 Borsi et al., 1995). The complete type III repeat ED-B, also known as the extratype III repeat B (EIIIB), may be entirely included or omitted in the FN molecule (20 Zardi et al., 1987). ED-B is highly conserved in different species, having 100% homology in all mammalians thus far studied (human, rat, mouse, dog) and 96% homology with a similar domain in chicken. The FN isoform containing ED-B (B-FN) is undetectable immunohistochemically in normal adult tissues, with the exception of tissues undergoing physiological remodeling (e.g., endometrium and ovary) and during wound healing (17 Carnemolla et al., 1989; 21 ffrench-Constant, et al., 1989). By contrast, its expression in tumors and fetal tissues is high (17 Carnemolla et al, 1989). Furthermore, it has been demonstrated that B-FN is a marker of angiogenesis (22 Castellani et al., 1994) and that endothelial cells invading tumor tissues migrate along ECM fibers containing B-FN (23 Tarli et al. 1999).

Selective targeting of tumoral vasculature has been described using a human recombinant antibody, scFv(L19) (13 Pini et al., 98), specific for the B-FN isoform (24 Carnemolla et al., 1996; 23 Tarli et al., 99; 25 Viti et al., 99; 26 Neri et al., 97; 27 Demartis et al., 2001). The antibody may be used in both in vivo diagnostic (immunoscintigraphy) and therapeutic approaches entailing the selective delivery of therapeutic radionuclides or toxic agents to tumoral vasculature. In addition, Birchler et al. (28 1999) showed that scFv (L19), chemically coupled to a photosensitizer, selectively accumulates in the newly formed blood vessels of the angiogenic rabbit cornea model and, after irradiation with near infrared light, mediates complete and selective occlusion of ocular neovasculature.

More recently, Nilsson et al. (29 2001) reported that the immunoconjugate of scFv(L19) with the extracellular domain of tissue factor mediates selective infarction in different types of murine tumor models. Furthermore, fusion proteins of scFv(L19) and IL-2 or IL-12 have shown the enhanced therapeutic efficacy of these two cytokines (30 Halin et al., submitted; 31 Carnemolla et al., 2002). See also, WO01/62298 for use of fusions in treatment of lesions of pathological angiogenesis, including tumors. Finally, since L19 reacts equally well with mouse and human ED-B, it can be used for both pre-clinical and clinical studies.

See also PCT/GB97/01412, PCT/EP99/03210, PCT/EP01/02062 and PCT/IB01/00382.

Different antibody formats have shown diverse behavior in terms of in vivo stability, clearance and performance in tumor targeting (32 Wu et al., 2000). A mini-immunoglobulin or small immunoprotein (SIP) is described in (33 Li et al., 1997).

The present invention is based on preparation of, characterization of and investigation of the in vivo biodistribution of L19 human antibody molecules in different formats, namely, scFv, mini-immunoglobulin and complete IgG1.

The volume (mm³) is plotted versus time (days). Each data point is the average of six mice±SD.

FIG. 3 shows the results of size exclusion chromatography on the different L19 formats. In panels A, B and C are shown size exclusion chromatography (SUPERDEX™ 200) profiles of the L19 formats scFv, mini-immunoglobulin and IgG1, respectively, after radioiodination. Panels D, E and F show size exclusion chromatography (SUPERDEX™ 200) profiles of plasma at the indicated times after i.v. injection of the radioiodinated L19 formats, scFv, mini-immunoglobulin and IgG1, respectively. No changes in the curve profiles of L19-SIP or L19-IgG1 were detected when loading plasma at different times after injection, while 3 h after L19(scFv)2 injection a second peak of higher molecular mass was observed.

Figure 4A:
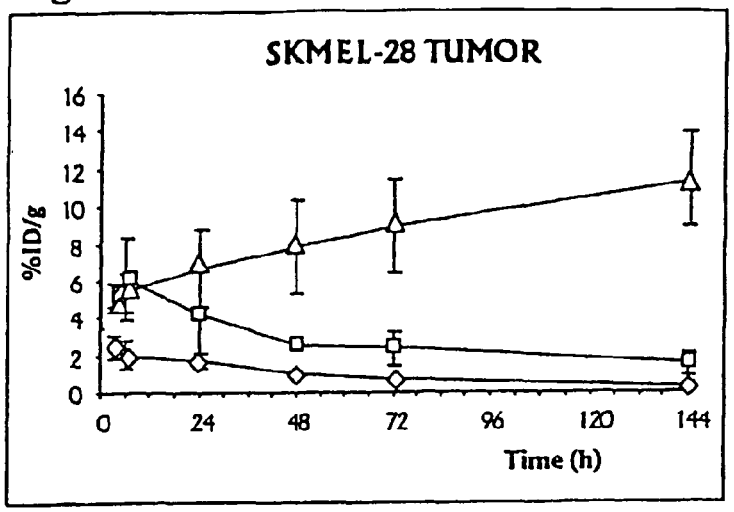
Figure 4B:
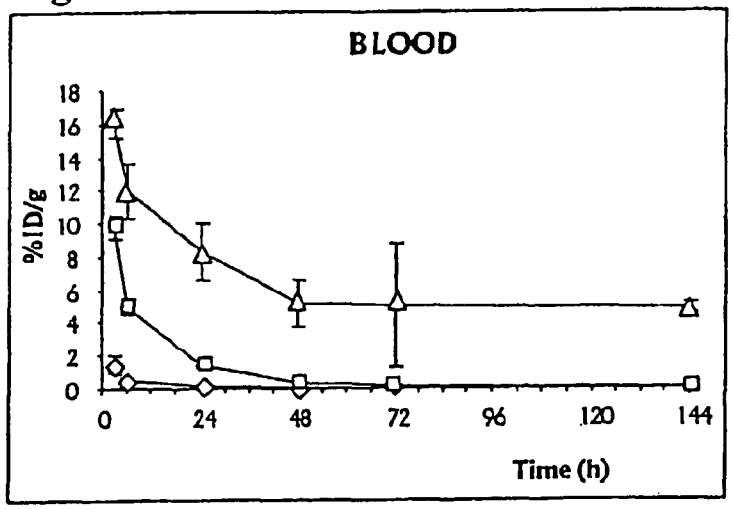
Figure 4C:
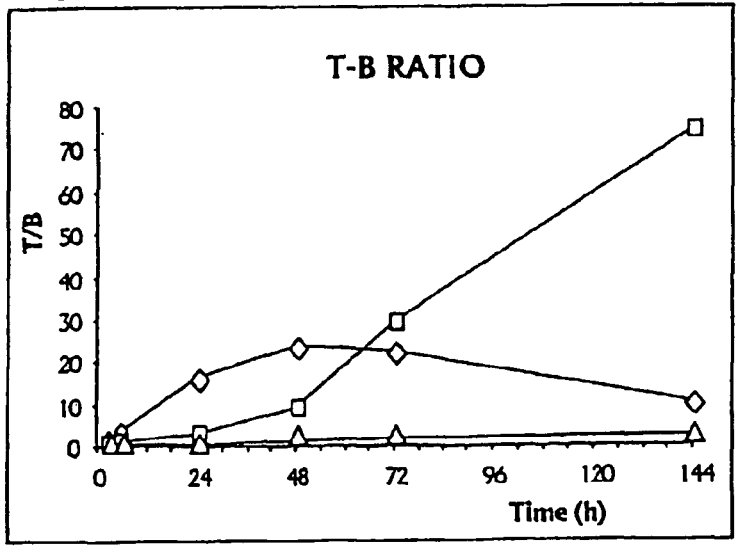

FIG. 4 shows results of biodistribution experiments in SK-MEL-28 tumor-bearing mice using different radioiodinated L19 antibody molecule formats. The variations of the % ID/g in the tumor (FIG. 4A) and in the blood (FIG. 4B) at the indicated times after i.v. injection are reported. In FIG. 4C the tumor-blood ratios of the % ID/g are plotted. The curves of L19(scFv) are indicated by diamonds, of L19 mini-immunoglobulin by squares and of L19 IgG1 by triangles.

Figure 5A:
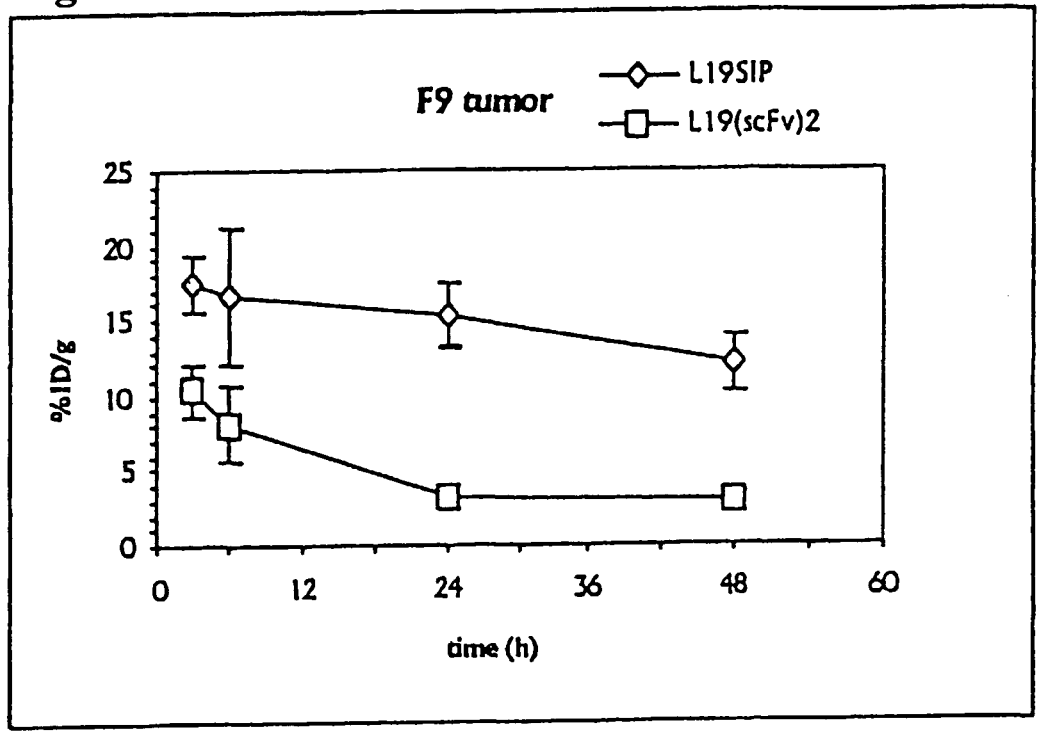
Figure 5B:
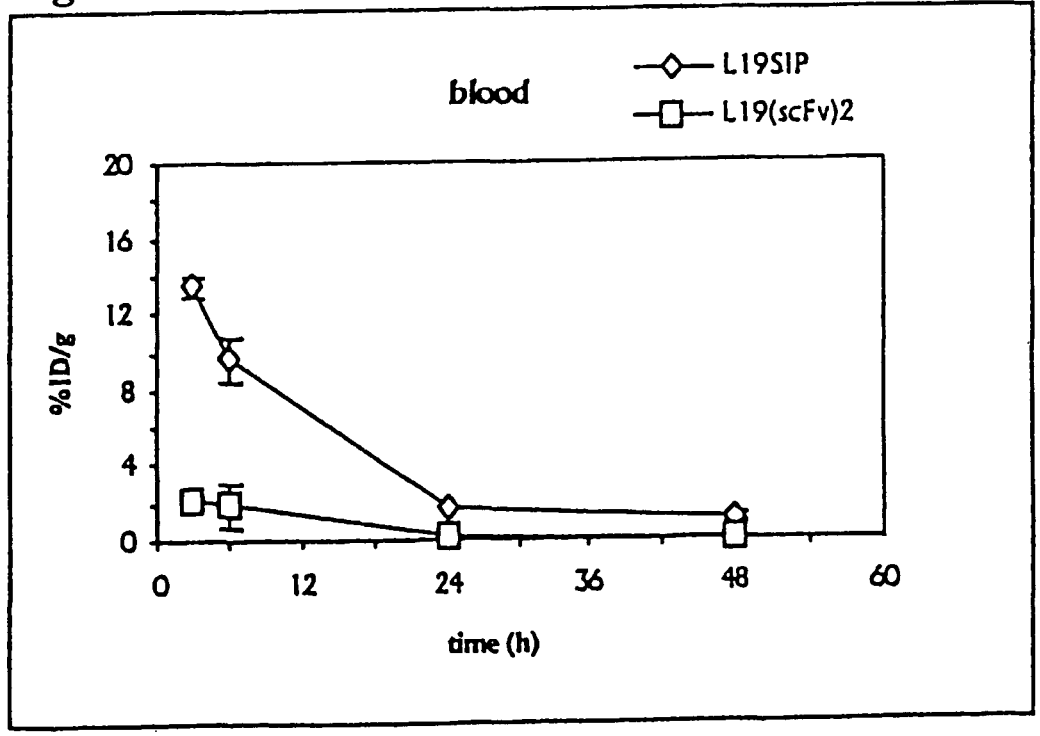

FIG. 5 shows results of biodistribution experiments in F9 tumor-bearing mice using radioiodinated L19(scFv) (squares) and L19 mini-immunoglobulin (diamonds). The variations of the % ID/g in the tumor (A) and in the blood (B), at the indicated different times after i.v. injection are reported.

In one aspect, the present invention provides a specific binding member which binds human ED-B of fibronectin and which comprises the L19 VH domain and a VL domain, optionally the L19 VL domain, and wherein the specific binding member comprises a mini-immunoglobulin comprising said antibody VH domain and antibody VL domain fused to $\epsilon_{S2}$-CH4 and dimerized or comprises a whole IgG1 antibody molecule.

The L19 VH domain (SEQ ID NO: 14) and L19 VL domain (SEQ ID NO: 15) sequences are set out in Pini et al. (1998) J. Biol. Chem. 273: 21769-21776, those sequences being fully incorporated herein by reference to Pini et al. as if set out here.

Generally, a VH domain is paired with a VL domain to provide an antibody antigen binding site. In a preferred embodiment, the L19 VH domain is paired with the L19 VL domain, so that an antibody antigen binding site is formed comprising both the L19 VH and VL domains. In other embodiments, the L19 VH is paired with a VL domain other than the L19 VL. Light-chain promiscuity is well established in the art.

One or more CDRs may be taken from the L19 VH or VL domain and incorporated into a suitable framework. This is discussed further below. L19 VH CDR's 1, 2 and 3 are shown in SEQ ID NOS 1, 2, and 3, respectively. L19 VL CDR's 1, 2 and 3 are shown in SEQ ID NOS 4, 5 and 6, respectively.

Variants of the VH and VL domains and CDRs of which the sequences are set out herein and which can be employed in specific binding members for ED-B can be obtained by means of methods of sequence alteration or mutation and screening.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDR's.

A specific binding member according to the invention may be one which competes for binding to antigen with a specific binding member which both binds ED-B and comprises an antigen-binding site formed of the L19 VH domain and L19 VL domain. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus, further aspects of the present invention employ a specific binding member comprising a human antibody antigen-binding site which competes with L19 for binding to ED-B.

A specific binding member according to the present invention may bind ED-B with at least the affinity of L19, binding affinity of different specific binding members being compared under appropriate conditions.

In addition to antibody sequences, a specific binding member according to the present invention may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or enzyme (e.g. via a peptidyl bond or linker).

In treatment of disorders or lesions of pathological angiogenesis, a specific binding member of the invention may be conjugated to a toxic molecule, for instance a biocidal or cytotoxic molecule that may be selected from interleukin-2 (IL-2), doxorubicin, interleukin-12 (IL-12), Interferon-γ (IFN-γ), Tumor Necrosis Factor α (TNFα) and tissue factor (preferably truncated tissue factor, e.g. to residues 1-219). See e.g. WO01/62298.

In further aspects, the invention provides an isolated nucleic acid which comprises a sequence encoding a specific binding member according to the present invention, and methods of preparing a specific binding member which comprise expressing said nucleic acid under conditions to bring about production of said specific binding member and recovering it.

Specific binding members according to the invention may be used in a method of treatment or diagnosis of the human or animal body, such as a method of treatment (which may include prophylactic treatment) of a disease or disorder in a human patient which comprises administering to said patient an effective amount of a specific binding member of the invention. Conditions treatable in accordance with the present invention include tumors, especially solid tumors, and other lesions of pathological angiogenesis, including, rheumatoid arthritis, diabetic retinopathy, age-related macular degeneration, and angiomas.

A yet further aspect provides a method of producing a specific binding member of the invention, the method comprising causing expression from encoding nucleic acid. Such a method may comprise culturing host cells under conditions for production of said specific binding member.

A method of production may comprise a step of isolation and/or purification of the product.

A method of production may comprise formulating the product into a composition including at least one additional component, such as a pharmaceutically acceptable excipient.

These and other aspects of the invention are described in further detail below.

TERMINOLOGY

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody Molecule

This describes an immunoglobulin whether natural or partly or wholly synthetically produced. The term also covers any polypeptide or protein comprising an antibody binding domain. Antibody fragments which comprise an antigen binding domain are such as Fab, scFv, Fv, dAb, Fd; and diabodies. The present invention is concerned with whole IgG1 antibody molecules and mini-immunoglobulins comprising $\epsilon_{S2}$-CH4 as disclosed.

Techniques of recombinant DNA technology may be used to produce from an initial antibody molecule other antibody molecules which retain the specificity of the original antibody molecule. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400.

As antibodies can be modified in a number of ways, the term "antibody molecule" should be construed as covering any specific binding member or substance having an antibody antigen-binding domain with the required specificity. Thus, this term covers antibody fragments and derivatives, including any polypeptide comprising an immunoglobulin antigen-binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

Antigen Binding Domain

This describes the part of an antibody molecule which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

Isolated

This refers to the state in which specific binding members of the invention, or nucleic acid encoding such binding members, will generally be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, substitutions may be made in the CDR and/or VH or VL domain.

The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 5th Edition. US Department of Health and Human Services. 1991, and updates thereof, now available on the Internet (http://immuno.bme.nwu.edu or find "Kabat" using any search engine).

Preferably, a CDR amino acid sequence substantially as set out herein is carried as a CDR in a human variable domain or a substantial portion thereof. The L19 VH CDR3 and/or L19 VL CDR3 sequences substantially as set out herein may be used in preferred embodiments of the present invention and it is preferred that each of these is carried as a CDR3 in a human heavy or light chain variable domain, as the case may be, or a substantial portion thereof.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains or protein labels as discussed in more details below.

In an IgG1 antibody molecule according to the present invention, VL domains may be attached at the C-terminal end to antibody light chain constant domains including human Cκ or Cλ chains, preferably Cκ chains.

Specific binding members of the invention may be labelled with a detectable or functional label. Detectable labels are described below and include radiolabels such as radioisotopes of Technetium, Indium, Yttrium, Copper, Lutetium or Rhenium, in particular $^{94m}$Tc, $^{99m}$Tc, $^{186}$Re, $^{188}$Re, $^{111}$In, $^{86}$Y, $^{88}$Y, $^{177}$Lu, $^{64}$Cu and $^{67}$Cu, which may be attached to antibodies of the invention using conventional chemistry known in the art of antibody imaging as described herein.

Labels also include enzyme labels such as horseradish peroxidase. Labels further include chemical moieties such as biotin which may be detected via binding to a specific cognate detectable moiety, e.g. labelled avidin.

The specific binding members (L19-SIP) disclosed herein are particularly well suited for radiolabeling with isotopes such as $^{94m}$Tc, $^{99m}$Tc, $^{186}$Re, $^{188}$Re, $^{203}$Pb, $^{67}$Ga, $^{68}$Ga, $^{47}$Sc, $^{110m}$In, $^{111}$In, $^{97}$Ru, $^{62}$Cu, $^{64}$Cu, $^{67}$Cu, $^{68}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{72}$Lu and $^{18}$F, and subsequent use in radio-diagnosis and radiotherapy. $^{99m}$Tc is a particularly preferred radioisotope for labelling, and a suitable protocol is described in the experimental section below.

To radiolabel the specific binding members directly, the cysteine bridged molecules are first reduced by an appropriate reducing agent e.g. stannous(II)chloride, Tris(2-carboxyethyl)phosphine (TCEP) generating free cysteine SH-groups that can react with isotopes e.g. Tc or Re. In this particular procedure, the permetalates obtained from an instant generator system are reduced by a reducing agent e.g. stannous(II) chloride in the presence of an auxiliary ligand e.g. sodium tartrate and the API (details are provided below in the experimental section).

Indirect labeling with e.g. indium, yttrium, lanthanides or technetium and rhenium may be performed by pre-conjugating a chelating ligand, preferably derived from ethylene diamine tetraacetic acid (EDTA), diethylene triamine pentaacetic acid (DTPA), cyclohexyl 1,2-diamine tetraacetic acid (CDTA), ethyleneglycol-O,O'-bis(2-aminoethyl)-N,N,N',N'-diacetic acid (HBED), triethylene tetraamine hexaacetic acid (TTHA), 1,4,7,10-tetraazacyclododecane-N,N',N'''-tetraacetic acid (DOTA), 1,4,7-triazacyclononane-N,N',N''-triacetic acid (NOTA), 1,4,8,11-tetraazacyclotetradecane-N,N',N'', N'''-tetraacetic acid (TETA), mercaptoacetyl diglycine (MAG$_2$), mercaptoacetyl triglycine (MAG$_3$), mercaptoacetyl glycyl cysteine (MAGC), cysteinyl glycyl cysteine (CGC) to either amine or thiol groups of the specific binding member. The chelating ligands possess a suitable coupling group e.g. active esters, maleimides, thiocarbamates or α-halogenated acetamide moieties. For conjugating chelating ligands to amine groups e.g. ϵ-NH$_2$-groups of lysine residues previous reduction of the L-19-SIP compound is not required.

Specific binding members of the present invention are designed to be used in methods of diagnosis or treatment in human or animal subjects, preferably human.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

Clinical indications in which a specific binding member of the invention may be used to provide therapeutic benefit include tumors such as any solid tumor, also other lesions of pathological angiogenesis, including rheumatoid arthritis, diabetic retinopathy, age-related macular degeneration, and angiomas.

Specific binding members according to the invention may be used in a method of treatment of the human or animal body, such as a method of treatment (which may include prophylactic treatment) of a disease or disorder in a human patient which comprises administering to said patient an effective amount of a specific binding member of the invention. Conditions treatable in accordance with the present invention are discussed elsewhere herein.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int J. Cancer 47: 659-664; Bagshawe K. D. et al. (1991) Antibody, Immunoconjugates and Radiopharmaceuticals 4: 915-922.

A composition may be administered alone or in combination with other treatments, either simultaneously or sequentially dependent upon the condition to be treated.

Specific binding members of the present invention, including those comprising an antibody antigen-binding domain, may be administered to a patient in need of treatment via any suitable route, usually by injection into the bloodstream and/ or directly into the site to be treated, e.g. tumor. The precise dose will depend upon a number of factors, the route of treatment, the size and location of the area to be treated (e.g. tumor), the precise nature of the antibody (e.g. whole IgG1 antibody molecule, mini-immunoglobulin molecule), and the nature of any detectable label or other molecule attached to the antibody molecule. A typical antibody dose will be in the range 10-50 mg.

This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine, or anti-emetics.

The present invention provides a method comprising causing or allowing binding of a specific binding member as provided herein to ED-B. As noted, such binding may take place in vivo, e.g. following administration of a specific binding member, or nucleic acid encoding a specific binding member, or it may take place in vitro, for example in ELISA, Western blotting, immunocytochemistry, immuno-precipitation or affinity chromatography.

The amount of binding of specific binding member to ED-B may be determined. Quantitation may be related to the amount of the antigen in a test sample, which may be of diagnostic interest, which may be of diagnostic interest.

The reactivities of antibodies on a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention further extends to a specific binding member which competes for binding to ED-B with any specific binding member which both binds the antigen and comprises a V domain including a CDR with amino acid substantially as set out herein, preferably a VH domain comprising VH CDR3 of SEQ ID NO. 3. Competition between binding members may be assayed easily in vitro, for example by tagging a specific reporter molecule to one binding member which can be detected in the presence of other untagged binding member(s), to enable identification of specific binding members which bind the same epitope or an overlapping epitope. Competition may be determined for example using the ELISA as described in Carnemolla et al. (24 1996).

The present invention further provides an isolated nucleic acid encoding a specific binding member of the present invention. Nucleic acid may be DNA or RNA.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding a specific binding member as provided itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antibody fragments in prokaryotic cells such as E. coli is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 3nd edition, Sambrook et al., 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Further aspects and embodiments of the present invention will be apparent to those skilled in the art in the light of the present disclosure including the following experimental exemplification.

All documents mentioned anywhere in this specification and incorporated by reference.

EXPERIMENTAL EXEMPLIFICATION OF ASPECTS AND EMBODIMENTS OF THE PRESENT INVENTION

Figure 1A:
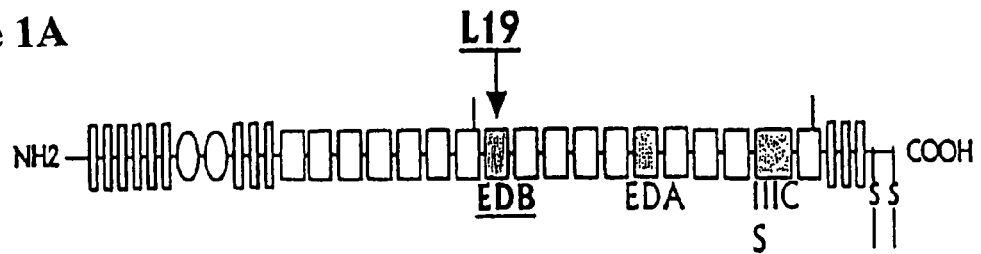
FIG. 1 shows models illustrating the structures of different proteins. A: Model of the domain structure of a FN subunit. The protein sequences undergoing alternative splicing are indicated in grey. As indicated, the epitope of the recombinant antibody L19 is localized within the repeat ED-B. B-D: Schemes of the constructs used to express, respectively, L19 (scFv) (B); L19-SIP (C); and L19-IgG1/κ (D).
Figure 1B:
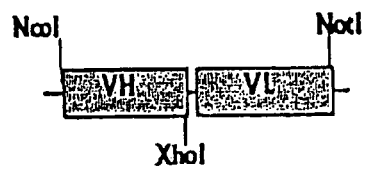

Materials and Methods
Preparation and Expression of scFv, Small Immunoprotein (SIP) and IgG1 Constructs scFv The scFv(L19) (FIG. 1A) is an affinity matured (Kd=5.4× $10^{-11}$ M) antibody fragment specifically directed against the ED-B domain of fibronectin (13 Pini et al., 1998). The scFv (D1.3) (7 McCafferty et al.; 26 Neri et al., 1997), a mouse-anti-hen egg white lysozyme scFv, was used as a control. These scFvs were expressed in *E. Coli* strain HB2151 (Maxim Biotech, San Francisco Calif.) according to Pini et al. (34 1997).

Mini-Immunoglobulin

Figure 1C:
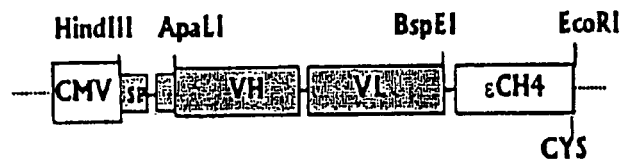
Figure 1D:
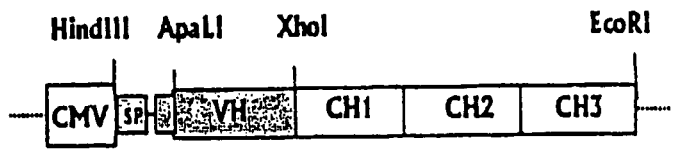
Figure 1D:
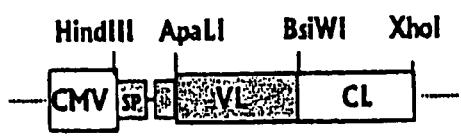

To construct the L19 small immunoprotein (L19-SIP) gene (FIG. 1C) the DNA sequence coding for the scFv(L19) was amplified by Polymerase Chain Reaction (PCR) using Pwo DNA Polymerase (Roche), according to manufacturer's recommendations, with primers BC-618 (gtgtgcactcggaggtg-cagctgttggagtctggg—SEQ ID NO. 8) and BC-619 (gcctccg-gatttgatttccaccttggtcccttggcc—SEQ ID NO. 9), containing ApaLI and BspEI restriction sites, respectively. The amplification product was inserted ApaLI/BspEI in the pUT-εSIP vector, which provides the scFv gene with a secretion signal, required for secretion of proteins in the extracellular medium. The pUT-εSIP vector was obtained from the previously described pUT-SIP-long (33 Li et al., 1997) after substituting the human constant γ1-CH3 domain with the CH4 domain of the human IgE secretory isoform IgE-S2 ($\epsilon_{S2}$-CH4; 35 Batista et al., 1996). CH4 is the domain that allows dimerization in the IgE molecule and the $\epsilon_{S2}$ isoform contains a cysteine at the carboxyterminal end, which stabilizes the IgE dimer through an inter-chain disulphide bond. In the final SIP molecule the ScFv(L19) was connected to the $\epsilon_{S2}$-CH4 domain by a short GGSG linker. The SIP gene was then excised from the plasmid pUT-εSIP-L19 with HindIII and EcoRI restriction enzymes and cloned into the mammalian expression vector pcDNA3 (Invitrogen, Groningen, The Netherlands), which contains the Cytomegalovirus (CMV) promoter, in order to obtain the construct pcDNA3-L19-SIP.

The DNA sequence coding for scFv(D1.3) was amplified using the primers BC-721 (ctcgtgcactcgcaggtgcagctgcag-gagtca—SEQ ID NO. 10) and BC-732 (ctctccggac-cgtttgatctcgcgcttggt—SEQ ID NO. 11) and inserted ApaLI/BspEI in the pUT-εSIP vector. The D1.3-SIP gene was then excised from the pUT-εSIP-D1.3 with HindIII and EcoRI restriction enzymes and cloned into pcDNA3, in order to obtain the construct pcDNA3-D1.3-SIP.

These constructs were used to transfect SP2/0 murine myeloma cells (ATCC, American Type Culture Collection, Rockville, Md., USA) using FUGENE™ 6 Transfection Reagent (Roche), following the protocol for adherent cells, optimized by the manufacturer. Transfectomas were grown in DMEM supplemented with 10% FCS and selected using 750 μg/ml of Geneticin (G418, Calbiochem, San Diego, Calif.). IgG1

To prepare complete IgG1, the variable region of the L19 heavy chain (L19-VH), together with its secretion peptide sequence, was excised with HindIII and XhoI from the previously described L19-pUTεSIP and inserted in the pUC-IgG1 vector, containing the complete human γ1 constant heavy chain gene. The recombinant IgG1 gene was then excised from the pUC-IgG1-L19-VH with HindIII and EcoRI and cloned into pcDNA3, to obtain the construct pcDNA3-L19-IgG1.

For the preparation of the complete L19 light chain, L19-VL was amplified from the L19-pUT-εSIP (described above) by PCR using the primers BC-696 (tggtgtgcactcggaaattgtgt-tgacgcagtc—SEQ ID NO. 12) and BC-697 (ctctcg-tacgtttgatttccaccttggtcc—SEQ ID NO. 13), containing ApaLI and BsiWI restriction sites, respectively. After digestion with ApaLI and BsiWI, the amplification product was inserted in the vector pUT-SEC-hCκ containing the secretion signal sequence and the sequence of the human constant κ light chain. The recombinant light chain gene was then excised from pUT-SEC-hCκ-L19-VL with HindIII and XhoI and inserted in the pCMV2Δ□ mammalian expression vector, derived from a pcDNA3 vector by removing the resistance gene to G418, to obtain the construct pCMV2Δ-L19-κ.

Equimolar amounts of these constructs were used to cotransfect SP2/0 murine myeloma cells as described above. Geneticin selected clones were screened in ELISA for the ability to secrete chimeric immunoglobulin, complete of heavy and light chains.

All DNA constructs were purified using the Maxiprep system from Qiagen (Hilden, Germany), and the DNA sequences of both strands of the constructs were confirmed using the ABI PRISM™ dRhodamine Terminator Cycle Sequencing Ready Reaction Kit (Perkin Elmer, Foster City, Calif.). All restriction enzymes (RE) were from Roche Diagnostics (Milan, Italy), with the exception of BsiWI (New England Biolabs, Beverly, Mass.). After RE digestion, inserts and vectors were recovered from agarose gels using the QIAQUICK™ method (Qiagen).

Purification and Quality Control of Antibodies

Immunoaffinity chromatography was performed to purify the different antibodies according to the procedure described by Carnemolla et al. (24 1996).

ED-B conjugated to SEPHAROSE™ 4B (Amersham Pharmacia Biotech., Uppsala, Sweden) following manufacturer's instructions (24 Carnemolla et al., 96) was used to immunopurify all different L19 antibody formats, while a column of hen egg white lysozyme (Sigma, St. Louis, USA) conjugated to SEPHAROSE™ 4B (Amersham Pharmacia) was used for D1.3 antibodies.

The immunopurified antibody formats L19-SIP and L19-IgG1 required no further purification and were dialyzed against PBS, pH 7.4, at +4° C. Since scFvs obtained from immunoaffinity chromatography are made up of two forms, monomeric and dimeric, a second purification step, as described by Demartis et al. (27 2001), was required to isolate the latter form. Batches of the different antibody formats were prepared and analyzed using SDS-PAGE under reducing and non-reducing conditions, immunohistochemistry, size exclusion chromatography (SUPERDEX™ 200, Amersham Pharmacia Biotech) and ELISA experiments.

Sodium Dodecyl Sulfate-Polyacrylamide Gel Electrophoresis (SDS-PAGE), Enzyme Linked Immunoabsorbent Assay (ELISA), Size Exclusion Chromatography and Immunohistochemistry Screening ELISA experiments on the conditioned culture media were performed according to Carnemolla et al. (24 1996). To reveal the expression of the different L19 antibody formats, the recombinant fragment 7B89 (24 Carnemolla et al., 1996), containing the ED-B domain of FN, that includes the epitope recognized by the L19, was immobilized on Maxisorp immunoplates (Nunc, Roskilde, Denmark). To detect D1.3 antibodies in ELISA experiments, hen egg white chicken lysozyme (Sigma) was immobilized on NH2 surface EIA plates (Costar, Cambridge, Mass.). A peroxidase-conjugated rabbit anti human IgE (Pierce, Rockford, Ill.), diluted according to manufacturer's recommendations, was used as secondary antibody to detect SIPs. A peroxidase-conjugated rabbit anti human IgG (Pierce) was used in the case of IgG1. For the scFvs containing the tag sequence FLAG, a mouse anti-human FLAG monoclonal antibody (M2, Kodak) and a peroxidase-conjugated goat anti-mouse antibody (Pierce) were used as secondary and tertiary antibodies, respectively. In all cases the immunoreactivity with the immobilized antigen was detected using the substrate ABTS for peroxidase (Roche) and photometric absorbance at 405 nm was measured.

A SUPERDEX™ 200 (Amersham Pharmacia) chromatography column was used to analyze the gel filtration profiles of the purified antibodies under native conditions using fast protein liquid chromatography (FPLC; Amersham Pharmacia). Immunohistochemistry on different tissue cryostat sections was performed as described by Castellani et al. (22 1994) and 4-18% gradient SDS-PAGE was carried out according to Carnemolla et al. (17 1989) under reducing and non-reducing conditions.

Animals and Cell Lines

Athymic-nude mice (8 week-old nude/nude CD1 females) were obtained from Harlan Italy (Correzzana, Milano, Italy), 129 (clone SvHsd) strain mice (8-10 weeks old, female) were obtained from Harlan UK (Oxon, England). Mouse embryonal teratocarcinoma cells (F9), human melanoma derived cells (SK-MEL-28) and mouse myeloma cells (SP2/0) were purchased from American Type Culture Collection (Rockville, Md.). To induce tumors, nude mice were subcutaneously injected with $16 \times 10^6$ SK-MEL-28 cells, and 129 strain mice with $3 \times 10^6$ F9 cells. The tumor volume was determined with the following formula: $(d)^2 \times D \times 0.52$, where d and D are, respectively, the short and long dimensions (cm) of the tumor, measured with a caliper. Housing, treatments and sacrifice of animals were carried out according to national legislation (Italian law no. 116 of 27 Jan. 1992) regarding the protection of animals used for scientific purposes.

Radioiodination of Recombinant Antibodies

Radioiodination of proteins was achieved following the Chizzonite indirect method (36 Riske et al., 1991) using IODO-GEN Pre-coated Iodination tubes (Pierce) to activate $Na^{125}I$ (NEN Life Science Products, Boston, Mass.) according to manufacturer's recommendations. In the reported experiments, 1.0 mCi of $Na^{125}I$ was used for 0.5 mg of protein. The radiolabeled molecules were separated from free $^{125}$ using PD10 (Amersham Pharmacia) columns pre-treated with 0.25% BSA and equilibrated in PBS. The radioactivity of the samples was established using a Crystal γ-counter (Packard Instruments, Milano, Italy). The immunoreactivity assay of the radiolabeled protein was performed on a 200 μl ED-B SEPHAROSE™ column saturated with 0.25% BSA in PBS. A known amount of radioiodinated antibody, in 200γ1 of 0.25% BSA in PBS, was applied on top and allowed to enter the column. The column was then rinsed with 1.5 ml of 0.25% BSA in PBS to remove non-specifically bound antibodies. Finally, the immunoreactive bound material was eluted using 1.5 ml of 0.1M TEA, pH11. The radioactivity of unbound and bound material was counted and the percentage of immunoreactive antibodies was calculated. Immunoreactivity was always higher than 90%.

Figure 3A:
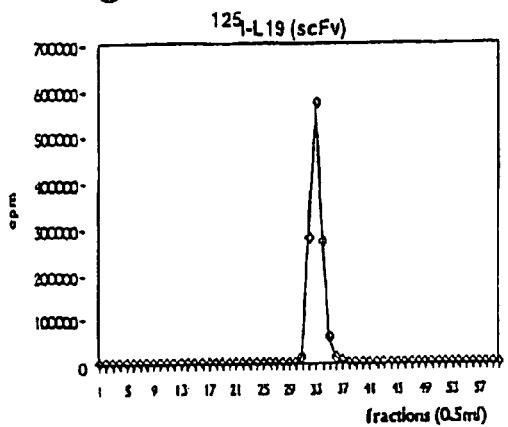
Figure 3B:
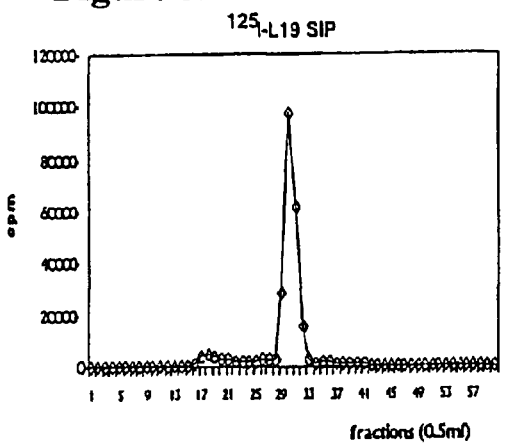
Figure 3C:
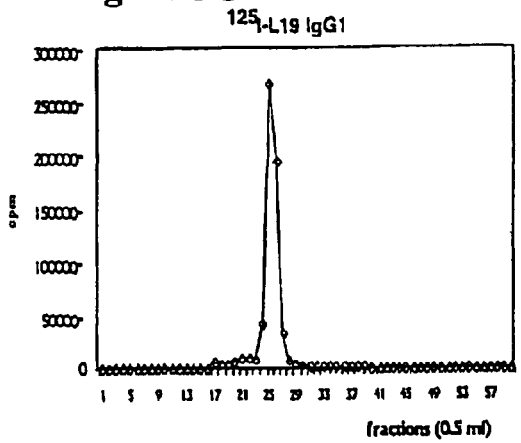
Figure 3D:
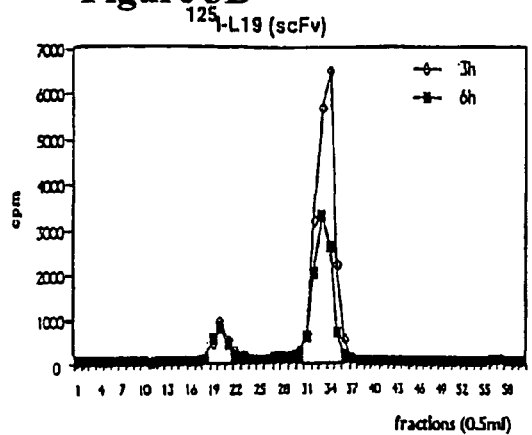
Figure 3E:
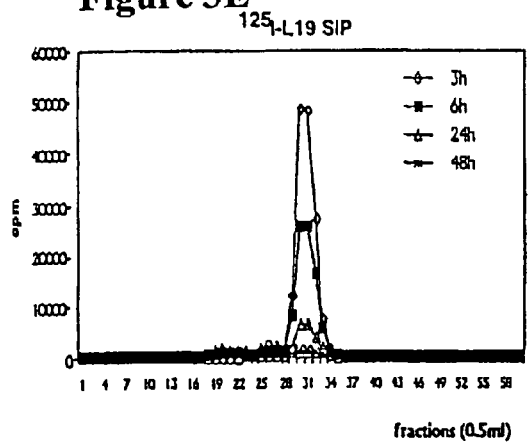
Figure 3F:
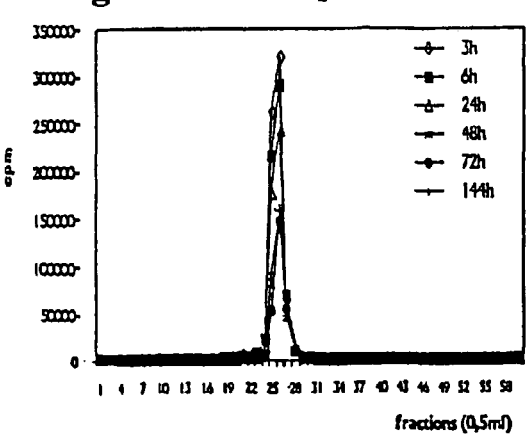

To further analyze the radioiodinated antibodies a known amount of radiolabeled protein in 200 μl was loaded onto the SUPERDEX™ 200 column. The retention volume of the different proteins did not vary after radioiodination. For the three radioiodinated L19 antibody formats and their negative controls, the radioactivity recovery from the SUPERDEX™ 200 column was 100% (FIGS. 3A, 3B and 3C).

Biodistribution Experiments

To block non-specific accumulation of $^{125}$ Iodine in the stomach and concentration in thyroid, 30 minutes before injection of the radiolabeled antibodies mice orally received 20 mg of sodium perchlorate (Carlo Erba, Italy) in water. This procedure was repeated at 24 h intervals for the duration of biodistribution experiments. Tumor-bearing mice were injected in the tail vein with 0.1 nmoles of the different radiolabeled antibodies (corresponding to 6 μg for scFvs, 8 μg for SIPs and 18 μg for IgGs) in 100 μl of saline. Three animals were sacrificed per time point, the different organs including tumor were excised, weighed, counted in a γ-counter and then fixed with 5% formaldehyde in PBS, pH 7.4, to be processed for microautoradiographies, performed according to Tarli et al. (23 1999).

The blood was sampled also for plasma preparation to determine the stability of the radiolabeled molecules in the blood stream using the already described immunoreactivity test and the gel filtration analysis. In both cases 200 μl of plasma were used. The radioactive content of the different organs was expressed as percentage of injected dose per gram (% ID/g). The blood clearance parameters of the radioiodinated antibodies was fitted with a least squares minimization procedure, using the MacIntosh Program Kaleidagraph (Synergy Software, Reading Pa., USA) and the equation:

$$X(t)=A\exp(-(\alpha t))+B\exp(-(\beta t))$$

where X (t) is the % ID/g of radiolabeled antibody at time t. This equation describes a bi-exponential blood clearance profile, in which the amplitude of the alpha phase is defined as A×100/(A+B) and the amplitude of the beta elimination phase is defined as B×100/(A+B). Alpha and beta are rate parameters related to the half-lives of the corresponding blood clearance phases. T1/2 (alpha phase)=ln2/alpha=0.692 .../alpha T1/2 (beta phase)=ln2/alpha=0.692 .../alpha. X(0) was assumed to be equal to 40%, corresponding to a blood volume of 2.5 ml in each mouse.

Results

Antibody Preparation

Using the variable regions of L19 (13 Pini et al., 1998) different antibody formats (scFv, mini-immunoglobulin and complete human IgG1) and their performance in vivo in targeting tumoral vasculature.

FIG. 1 shows the constructs used to express the different L19 antibody formats. Similar constructs were prepared using the variable regions of the scFv specific for a non-relevant antigen (D1.3; 7 McCafferty; 26 Neri et al., 1997).

To obtain SIPs and IgG1, SP2/0 murine myeloma cells were transfected with the constructs shown in FIG. 1 and stable transfectomas were selected using G418. The best producers were determined by ELISA and these clones were expanded for antibody purification. The purification of all three L19 antibody formats was based on immunoaffinity chromatography using recombinant ED-B conjugated to SEPHAROSE™. The yields were of about 8 mg/l for scFv (L19), 10 mg/l for L19-SIP, 3 mg/l for L19-IgG1. For the control proteins were used scFv(D1.3) specific for hen-egg lysozyme, and, using the variable regions of scFv D1.3, D1.3-SIP was constructed. These two antibodies were purified on hen-egg lysozyme conjugated to SEPHAROSE™. The yields were of 8 and 5 mg/l, respectively. As control for L19-IgG1 we used commercially available human IgG1/κ (Sigma).

SDS-PAGE analysis of the three purified L19 formats was performed, under both reducing and non-reducing conditions. For scFv(L19), the apparent mass was, as expected, about 28 kDa under both reducing and non-reducing conditions (not shown). The L19-SIP showed a molecular mass of nearly 80 kDa under non-reducing conditions, and had a mass of about 40 kDa under reducing conditions. The results demonstrated that more than 95% of the native molecule exists as a covalently-linked dimer. L19-IgG1 showed, as expected, a main band of about 180 kDa under non-reducing conditions, while, under reducing conditions, it showed two bands corresponding to the heavy chain of about 55 kDa and the light chain of about 28 kDa. Elution profiles of the three L19 antibody formats analyzed by size exclusion chromatography (SUPERDEX™ 200) were obtained. In all three cases a single peak with a normal distribution, and representing more than 98%, was detected. Using a standard calibration curve, the apparent molecular masses were 60 kDa for scFv(L19)$_2$, 80 kDa for L19-SIP and 180 kDa for L19-IgG1. In addition, molecular aggregates that are often present in recombinant protein preparations and that may invalidate the results obtained in in vivo studies were demonstrated to be absent. SDS-PAGE and size exclusion chromatography (SUPERDEX™ 200) performed on the purified control proteins gave similar results.

Using these three different L19 antibody formats, immunohistochemical analyses were performed on cryostat sections of SK-MEL-28 human melanoma induced in nude mice, and of F9 murine teratocarcinoma induced in 129 strain mice. Optimal results were obtained at concentrations as low as 0.25-0.5 nM. All three purified L19 antibodies recognized identical structures.

In Vivo Stability of the Radiolabeled L19 Antibody Formats

Figure 2:
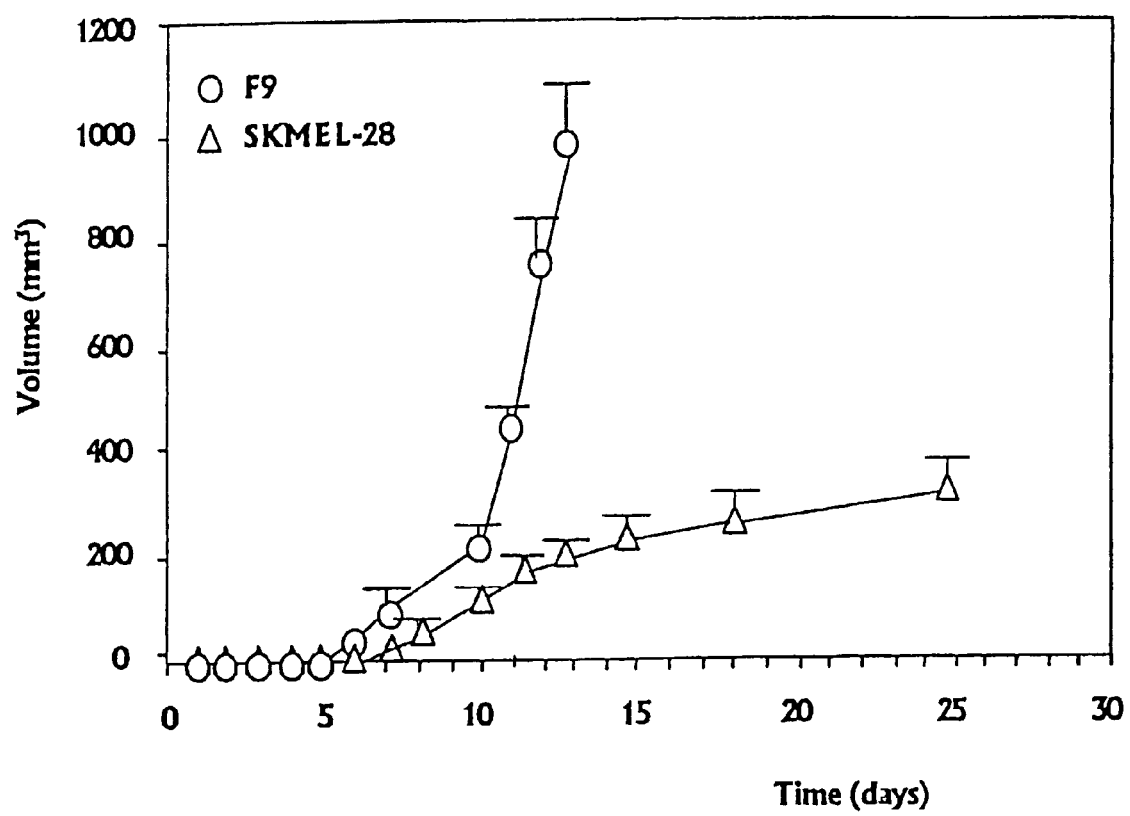
FIG. 2 shows growth curves of SK-MEL-28 tumor in nude mice (triangles) and of F9 tumor in 129 mouse strain (circles).

For in vivo biodistribution studies, SK-MEL-28 human melanoma and F9 murine teratocarcinoma were used. SK-MEL-28 tumor has a relatively slow growth rate while, F9 tumor grows rapidly (FIG. 2). Therefore, the use of SK-MEL-28 tumor enabled long-lasting experiments (up to 144 h), while F9 tumor was induced for short biodistribution studies (up to 48 h). All the biodistribution experiments were performed when the tumors were approximately 0.1-0.3 cm$^3$. For comparison of the various antibody formats, equimolar amounts (0.1 nmol) in 100 μl of sterile saline were injected. Before injection, the radioiodinated compounds were filtered 0.22 μm and the immunoreactivity and gel filtration profile were checked (see Materials and Methods). Immunoreactivity of the radiolabeled proteins was always more than 90%.

FIG. 3 A-C reports the profiles of the gel filtration analysis (SUPERDEX™ 200) of the radioiodinated L19 antibody formats.

Blood samples were taken from treated animals at the different time intervals from injection and the radioactivity present in plasma was analyzed for immunoreactivity and by gel filtration chromatography. Gel filtration profiles showed a single major peak, having the molecular mass of the injected protein, for all three L19 antibody formats. Only the profile of the scFv revealed a second peak having a higher molecular mass, suggesting formation of aggregates (FIG. 3 D-F). Furthermore, the formation of large molecular mass aggregates not eluting from the SUPERDEX™ 200 column, was observed for scFv(L19)2. In fact, while the recovery from the SUPERDEX™ 200 column was 90-100% of the applied radioactivity for both L19-SIP and L19-IgG, the yield of the loaded radioactivity of scFv(L19)2 was about 55%. The retained radioactivity was recovered only after washing the chromatography column with 0.5M NaOH, demonstrating that large aggregates were blocked on the column filter (Table 1).

Table 1 also reports the results of the immunoreactivity test performed on plasma (see Materials and Methods). Over the time of the experiments, L19-SIP and L19-IgG1 maintained the same immunoreactivity in plasma as the starting reagents. On the contrary, already 3 hours after injection the immunoreactivity of scFv(L19)2 in plasma was reduced to less than 40%.

Comparative Biodistribution Experiments

Tables 2 a, b, c and FIG. 4 report the results obtained in the biodistribution experiments with the radiolabeled L19 antibodies in SK-MEL-28 tumor bearing mice.

Tables 2 a,b,c show, at different times from i.v. injection of the radiolabeled antibodies, the average (±SD) of the % ID/g of tissues and organs, including tumors.

In FIG. 4 are depicted the variations of the % ID/g of the different antibody formats in tumor (A) and blood (B) at the different times of the experiments, as well as the ratios (C) between the % ID/g in tumor and blood. All three L19 antibody formats selectively accumulated in the tumor and the ratio of the % ID/g of tumor and other organs are reported in Table 3.

As demonstrated by microautoradiography, the antibodies accumulate only on the tumor vasculature, whereas no specific accumulation on the vasculature of normal organs was seen. By contrast, no specific accumulation of the radioiodinated control molecules in either tumors or normal tissues was found (Tables 2 a, b, c).

All three L19 antibody formats showed a clearance that was mediated mainly by the kidney, as determined by counting the urine samples. As expected, clearance rate was faster for scFv(L19)2 and slower for the complete L19-IgG1. Fitting of the curve with a biexponential function yielded the half-live values reported in Table 4.

FIG. 5 depicts the variations in the % ID/g (±SD) of tumor and blood obtained with the radioiodinated scFv(L19)2 and L19-SIP using the F9 teratocarcinoma tumor model. Due to the high angiogenic activity of F9 teratocarcinoma, accumulation of radioactive molecules in this tumor was 3 to 4 times higher, 3 and 6 h after i.v. injection than in SK-MEL-28 tumor and was persistently higher for the 48 h duration of the experiment. As for SK-MEL-28 tumor, specific accumulation in tumor vasculature was confirmed by microautoradiography, while no specific tumor accumulation was seen after injection of the control molecules. In Table 5 are reported the % ID/g of L19(scFv) and L19SIP, at different times after i.v. injection, in F9 tumors and other organs.

Synthesis of Reduced L19-SIP

To a solution of 375 µg (5 nmol) L19-SIP in 422 µl PBS were added 50 µl TCEP-solution (14.34 mg TCEP×HCl/5 ml aqueous $Na_2HPO_4$, 0.1M, pH=7.4). The reaction mixture was gently shaken for 1 h at 37° C. Reduced L19-SIP was purified by gel-chromatography using a NAP-5 column (Amersham, Eluant: PBS). SDS-PAGE analysis of the isolated product proofed the quantitative transformation of L19-SIP to reduced L19-SIP.

Yield: 100.3 µg/200 µl PBS (26.7%).

Synthesis of Tc-99m-L19-SIP 3.0 mg disodium-L-tartrate were placed in a vial followed by addition of 100.3 µg reduced L19-SIP in 200 µl PBS and the solution was diluted with 100 µl aqueous $Na_2HPO_4$-buffer (1M, pH=10.5). 85 µl Tc-99m generator eluate (24 h) and 10 µl $SnCl_2$-solution (5 mg $SnCl_2$/1 ml 0.1M HCl) were added. The reaction mixture was shaken for 0.5 h at 37° C. Tc-99m-labeled L19-SIP was purified by gel-chromatography using a NAP-5 column (Amersham, Eluant: PBS).

Radiochemical yield: 35.6%.
Radiochemical purity: 90.2% (SDS-PAGE).
Specific activity: 26.4 MBq/nmol.
Immunoreactivity: 91.4%

Synthesis of Tc-99m-$MAG_2$-L19-SIP Carboxy methyl-t-butyl disulfide

A solution of 21.75 ml (0.312 mol) 1-mercapto-acetic acid, 43.5 ml (0.312 mol) triethylamine and 100 g (0.312 mol) N-(tert.-butylthio)-N,N'-di-BOC-hydrazine in 1 l EtOH (abs.) was heated under reflux ($N_2$-atmosphere) for 60 h. EtOH was evaporated under reduced pressure to a final volume of about 200 ml. The residue was poured in 1.8 l $H_2O$ and the pH of the resulting suspension was adjusted to 7.14 using 5 molar NaOH. Di-BOC-hydrazine was filtered off and the pH of the resulting solution was adjusted to 2.2 using half-concentrated HCl. Crude material was extracted from water 3× with 600 ml $CH_2Cl_2$. The combined organic layers were dried over $MgSO_4$ and the solvent was evaporated under reduced pressure yielding 41.1 g (80%) as a yellow oil. The material was pure enough for further synthesis.

N-(benzyloxycarbonyl-Gly)Gly t-butyl ester (Z—(N-Gly)Gly t-butyl ester

A solution of 35.02 g (114 mmol) Z-Gly-OSuccinimide and 15 g (114 mmol) Gly-O-$^t$Bu in 1.41 $CH_2Cl_2$ was stirred under $N_2$-atmosphere at room temperature for 20 h. The organic layer was washed 3× with 250 ml 1% aqueous citric acid, 2× with 200 ml half-saturated aqueous $NaHCO_3$ and 1× with 200 ml water. The organic layer was dried over anhydrous $MgSO_4$. Evaporation of $CH_2Cl_2$ under reduced pressure yielded 36.5 g (99%) Z-Gly-Gly-O-$^t$Bu as a yellow oil. The crude material was pure enough for further synthesis.

Gly-Gly t-butyl ester 36.5 g (113 mmol) of Z-Gly-Gly-O$^t$Bu were dissolved in 1 l THF followed by the addition of 3.65 g palladium on charcoal (10%). The mixture was stirred under $H_2$ atmosphere (1 atm) for 3 h at room temperature. The suspension was purged with $N_2$, filtered (PTFE-filter: 0.45 µm) and the filtrate was concentrated under reduced pressure yielding 20.3 g (95%) Gly-Gly-O-$^t$Bu as a yellow oil. The crude material was pure enough for further synthesis.

Carboxy methyl-t-butyl disulfide glycyl glycine t-butyl ester

A solution of 23.85 g (115.6 mmol) DCC in 430 ml $CH_2Cl_2$ was dropwise added to a solution of 21.76 g (115.6 mmol) Gly-Gly-O-$^t$Bu, 20.84 g (115.6 mmol) Carboxy methyl-t-butyl disulfide and 13.3 g (115.6 mmol) NHS in 1 l $CH_2Cl_2$. The resulting suspension was stirred over night under $N_2$-atmosphere at room temperature. After filtration the resulting solution was washed 3× with 400 ml half-saturated aqueous $NaHCO_3$ and 1× with 400 ml water. The dried organic layer ($MgSO_4$) was evaporated under reduced pressure. The crude product was purified by chromatography on silica gel using a solvent gradient ranging from $CH_2Cl_2$/MeOH 99:1 to $CH_2Cl_2$/MeOH 98.5:1.5. 26.1 g (64%) were isolated as a yellow oil.

Mercaptoacetyl glycyl glycine 26.32 g (75.09 mmol) Carboxy methyl-t-butyl disulfide glycyl glycine t-butyl ester were dissolved in 233 ml TFA under $N_2$-atmosphere. The resulting solution was stirred for 20 min at room temperature. TFA was evaporated under reduced pressure ($5-10 \times 10^{-2}$ mbar) and the resulting oil was dried under stirring for additional 2 h ($5-10 \times 10^{-2}$ mbar). After addition of 250 ml $Et_2O$ a white powder precipitated and the suspension was stirred for 3 h. The material was filtered off and resuspended in 100 ml $Et_2O$. The resulting suspension was stirred over night, the product was filtered off and the material was dried at room temperature under reduced pressure yielding 20.46 g (92.5%) as a white powder.

Mercaptoacetyl glycyl glycine NHS ester

Mercaptoacetyl glycyl glycine (1 g, 3.4 mmol) and N-hydroxysuccinimide (391 mg, 3.4 mmol) are combined in a dry round bottom flask and dissolved in anhydrous DMF (4 ml). DCC (700 mg, 3.4 mmol) in anhydrous dioxane (2 ml) was added while stirring the reaction mixture. Within 15 min a precipitate (DCU) begins to form. After 1 h the precipitate is removed by vacuum filtration. The precipitate was washed with cold dioxane. The dioxane was removed from the filtrate. The product was precipitated from the remaining DMF solution by adding diethylether. The product was isolated by filtration, washed with cold diethylether, and dried in a vacuum desiccator overnight. Yield: 1.33 (99%).

Synthesis of Tc-99m-$MAG_2$-ε-HN(Lys)-L19-SIP

200 µg (2.66 nmol) non-reduced L19-SIP in 111 µl PBS were diluted with 300 µl of sodium borate buffer (0.1M, pH 8.5) and dialyzed 2×1 h with 200 ml of phosphate buffer (0.1M, pH 8.5) employing a SLIDE-A-LYZER™ 10,000 MWCO (Pierce Inc., Rockford, Ill., U.S.A.). 50 µl of mercaptoacetyl glycyl glycine NHS ester solution (0.50 mg dissolved in 500 µl of phosphate buffer, 0.1M, pH 8.5) were added and the reaction mixture was heated for 3 h at 37° C. The reaction mixture was dialyzed 2×1 h and 1×17 h (over night) with 200 ml of phosphate buffer (0.1M, pH 8.5) each, employing the SLIDE-A-LYZER™ 10,000 MWCO (Pierce Inc., Rockford, Ill., U.S.A.). 3.0 mg disodium-L-tartrate were added to the vial followed by addition of. 90 µl Tc-99m generator eluate (eluated daily) and 25 µl $SnCl_2$-solution (5 mg $SnCl_2$/1 ml 0.1M HCl) were added. The reaction mixture was shaken for 0.5 h at 37° C. Tc-99m-labeled L19-SIP was purified by gel-chromatography using a NAP-5 column (Amersham, Eluent: PBS).

Radiochemical yield: 55.1%.
Radiochemical purity: 94.5% (SDS-PAGE).
Specific activity: 15.2 MBq/nmol.
Immunoreactivity: 81.1%

Synthesis of Re-188-L19-SIP 3.0 mg disodium-L-tartrate were placed in a vial followed by addition of 150 µg reduced L19-SIP-SH in 310 µl PBS and the solution was diluted with 100 µl aqueous $Na_2HPO_4$-buffer (1M, pH=10.5). 100 µl Re-188 generator eluate and 50 µl $SnCl_2$-solution (5 mg $SnCl_2$/1 ml 0.1M HCl) were added. The reaction mixture was shaken for 1.5 h at 37° C. Re-188-labeled L19-SIP was purified by gel-chromatography using a NAP-5 column (Amersham, Eluent: PBS).

Radiochemical yield: 34.8%.
Radiochemical purity: 97.2% (SDS-PAGE).
Specific activity: 13.5 MBq/nmol.
Immunoreactivity: 91.7%

Synthesis of Reduced L19-SIP for Specific Conjugation of EDTA, CDTA, TETA, DTPA, TTHA, HBED, DOTA, NOTA, DO3A, and a like Type Chelators to the Cysteine-SH Group 50 µl TCEP-solution (14.34 mg TCEP×HCl/5 ml aqueous $Na_2HPO_4$, 0.1M, pH=7.4) were added to a solution of 375 µg (5 nmol) L19-SIP in 422 µl PBS. The reaction mixture was gently shaken for 1 h at 37° C. Reduced L19-SIP was purified by gel-chromatography using a NAP-5 column (Amersham, Eluent: sodium acetate buffer, 0.1M, pH 5.0). SDS-PAGE analysis of the isolated product proofed the quantitative transformation of L19-SIP into reduced L19-SIP.

Yield: 105.7 µg/200 µl (28.2%).

Synthesis of In-111-MX-DTPA-Maleimide-S(Cys)-L19-SIP-R (R=Reduced)

105 µg (2.8 nmol) reduced L19-SIP in 200 µl of sodium acetate buffer (0.1M, pH 5) were reacted with 50 µl of dissolved 1,4,7-triaza-2-(N-maleimido ethylene p-amino)benzyl-1,7-bis(carboxymethyl)-4-carboxymethyl 6-methyl heptane (0.25 mg DTPA-Maleimide in 500 µl sodium acetate buffer 0.1M pH 5) for 3 h at 37° C. The reaction mixture was dialyzed 2×1 h with 200 ml of sodium acetate buffer (0.1M, pH 6) employing a SLIDE-A-LYZER™ 10,000 MWCO (Pierce Inc., Rockford, Ill., U.S.A.).

80 µl [In-111]$InCl_3$ solution (HCl, 1N, 40 MBq, Amersham Inc.) were added and the reaction mixture was heated at 37° C. for 30 min.

In-111 labeled DTPA-Maleimide-S(Cys)-L19-SIP was purified by gel-chromatography using a NAP-5 column (Amersham, Eluent: PBS).

Radiochemical yield: 51.6%.
Radiochemical purity: 97.2% (SDS-PAGE).
Specific activity: 7.9 MBq/nmol.
Immunoreactivity: 88.5%

Synthesis of MX-DTPA-Maleimide (1,4,7-triaza-2-(N-maleimido ethylene p-amino)benzyl-1,7-bis(carboxymethyl)-4-carboxymethyl 6-methyl heptane)

512 mg (1 mmol) of {[3-(4-Amino-phenyl)-2-(bis-carboxymethyl-amino)-propyl]-[2-(bis-carboxymethyl-amino)-propyl]-amino}-acetic acid (Macrocyclics Inc. Dallas, Tex., U.S.A.) and 707 mg (7 mmol) triethylamine were dissolved in 3 ml dry DMF. 400 mg (1.5 mmol) of 3-(2,5-Dioxo-2,5-dihydro-pyrrol-1-yl)-propionic acid 2,5-dioxo-pyrrolidin-1-yl ester (Aldrich) in 1 ml dry DMF were added drop-wisely. The solution was stirred for 5 h at 50° C. 30 ml of diethylether were added slowly. The reaction mixture was stirred for further 30 min. The precipitate was collected by filtering. The crude product was purified by RP-HPLC (acetonitrile-:water-:trifluoracetic acid/3:96.9: 0.1→99.9:0:0.1). Yield: 61% (405 mg, 0.61 mmol). MS-ESI: 664=$M^+$+1.

Synthesis of In-111-MX-DTPA-ε-HN(Lys)-L19-SIP

200 µg (2.66 nmol) non-reduced L19-SIP in 111 µl PBS were diluted with 300 µl of sodium borate buffer (0.1M, pH 8.5) and dialyzed 2×1 h with 200 ml of sodium borate buffer (0.1M, pH 8.5) employing a SLIDE-A-LYZER™ 10,000 MWCO (Pierce Inc., Rockford, Ill., U.S.A.). 50 µl of 1,4,7-triaza-2-(p-isothiocyanato)benzyl-1,7-bis(carboxymethyl)-4-carboxymethyl-6-methyl heptane (MX-DTPA) solution (0.33 mg MX-DTPA dissolved in 500 µl of sodium borate buffer, 0.1M, pH 8.5) were added and the reaction mixture was heated for 3 h at 37° C. The reaction mixture was dialyzed 2×1 h and 1×17 h (over night) with 200 ml of sodium acetate buffer (0.1M, pH 6.0) each, employing the SLIDE-A-LYZER™ 10,000 MWCO (Pierce Inc., Rockford, Ill., U.S.A.).

80 µl [In-111]$InCl_3$ solution (HCl, 1N, 40 MBq, Amersham Inc.) were added and the reaction mixture was heated at 37° C. for 30 min. In-111 labeled MX-DTPA-ε-HN(Lys)-L19-SIP was purified by gel-chromatography using a NAP-5 column (Amersham, Eluent: PBS).

Radiochemical yield: 72.4%.
Radiochemical purity: 80.3% (SDS-PAGE).
Specific activity: 8.8 MBq/nmol.
Immunoreactivity: 77.5%

Synthesis of In-111-DOTA-C-Benzyl-p-NCS-ε-HN(Lys)-L19-SIP

200 µg (2.66 nmol) non-reduced L19-SIP in 108 µl PBS were diluted with 300 µl of sodium borate buffer (0.1M, pH 8.5) and dialyzed 2×1 h with 200 ml of sodium borate buffer (0.1M, pH 8.5) employing a SLIDE-A-LYZER™ 10,000 MWCO (Pierce Inc., Rockford, Ill., U.S.A.). 50 µl of 1,4,7,10-tetraaza-2-(p-isothiocyanato)benzyl cyclododecane-1,4,7,10-W tetraacetic acid (benzyl-p-SCN-DOTA, Macrocyclics Inc., Dallas Tex., U.S.A.) solution (1.5 mg benzyl-p-SCN-DOTA dissolved in 5 ml of sodium borate buffer, 0.1M, pH 8.5) were added to the solution and the reaction mixture was heated for 3 h at 37° C. The reaction mixture was dialyzed 2×1 h and 1×17 h (over night) with 200 ml of sodium acetate buffer (0.1M, pH 6.0) each, employing the SLIDE-A-LYZER™ 10,000 MWCO (Pierce Inc., Rockford, Ill., U.S.A.).

80 µl [In-111]InCl$_3$ solution (HCl, 1N, 40 MBq, Amersham Inc.) were added and the reaction mixture was heated at 37° C. for 30 min. In-111 labeled DOTA-C-Benzyl-p-NCS-ε-HN(Lys)-L19-SIP was purified by gel-chromatography using a NAP-5 column (Amersham, Eluent: PBS).

Radiochemical yield: 70.8%.
Radiochemical purity: 92.1% (SDS-PAGE).
Specific activity: 10.1 MBq/nmol.
Immunoreactivity: 75.1%

Synthesis of Y-88-MX-DTPA-ε-HN(Lys)-L19-SIP

200 µg (2.66 nmol) non-reduced L19-SIP in 110 µl PBS were diluted with 300 µl of sodium borate buffer (0.1M, pH 8.5) and dialyzed 2×1 h with 200 ml of sodium borate buffer (0.1M, pH 8.5) employing a SLIDE-A-LYZER™ 10,000 MWCO (Pierce Inc., Rockford, Ill., U.S.A.). 50 µl of MX-DTPA solution (0.33 mg MX-DTPA dissolved in 500 µl of sodium borate buffer, 0.1M, pH 8.5) were added and the reaction mixture was heated for 3 h at 37° C. The reaction mixture was dialyzed 2×1 h and 1×17 h (over night) with 200 ml of sodium acetate buffer (0.1M, pH 6.0) each, employing the SLIDE-A-LYZER™ 10,000 MWCO (Pierce Inc., Rockford, Ill., U.S.A.).

100 µl [Y-88]YCl$_3$ solution (HCl, 1N, 75 MBq, Oak Ridge National Lab.) were added and the reaction mixture was heated at 37° C. for 30 min. Y-88 labeled MX-DTPA-ε-HN(Lys)-L19-SIP was purified by gel-chromatography using a NAP-5 column (Amersham, Eluent: PBS).

Radiochemical yield: 68.1%.
Radiochemical purity: 91.5% (SDS-PAGE).
Specific activity: 11.4 MBq/nmol.
Immunoreactivity: 70.5%

Synthesis of Lu-177-DOTA-C-Benzyl-p-NCS-ε-HN(Lys)-L19-SIP

200 µg (2.66 nmol) non-reduced L19-SIP in 120 µl PBS were dissolved with 300 µl of sodium borate buffer (0.1M, pH 8.5) and dialyzed 2×1 h with 200 ml of sodium borate buffer (0.1M, pH 8.5) employing a SLIDE-A-LYZER™ 10,000 MWCO (Pierce Inc., Rockford, Ill., U.S.A.). 50 µl of benzyl-p-SCN-DOTA solution (1.5 mg dissolved in 5 ml of sodium borate buffer, 0.1M, pH 8.5) were added and the reaction mixture was heated for 3 h at 37° C. The reaction mixture was dialyzed 2×1 h and 1×17 h (over night) with 200 ml of sodium acetate buffer (0.1M, pH 6.0) each, employing the SLIDE-A-LYZER™ 10,000 MWCO (Pierce Inc., Rockford, Ill., U.S.A.).

200 µl [Lu-177]LuCl$_3$ solution (HCl, 1N, 80 MBq, NRH-Petten, Netherlands) were added and the reaction mixture was heated at 37° C. for 30 min. Lu-177 labeled DOTA-C-Benzyl-p-NCS-ε-HN(Lys)-L19-SIP was purified by gel-chromatography using a NAP-5 column (Amersham, Eluent: PBS).

Radiochemical yield: 72.2%.
Radiochemical purity: 94.9% (SDS-PAGE).
Specific activity: 18.3 MBq/nmol.
Immunoreactivity: 73.4%

Organ Distribution and Excretion of In-111-MX-DTPA-L19-SIP After a Single i.v. Injection into Tumour-Bearing Nude Mice The labeled peptides of the invention were injected intravenously in a dose of about 37 kBq into F9 (teratocarcinoma)-bearing animals (body weight about 25 g). The radioactivity concentration in various organs, and the radioactivity in the excreta, was measured using a γ counter at various times after administration of the substance.

The biodistribution of Ln-111-MX-DTPA-L19-SIP in F9 (teratocarcinoma)-bearing nude mice (mean±SD, n=3) is shown in Table 6.

Organ Distribution and Excretion of Tc-99m-L19-SIP After a Single i.v. Injection into Tumour-Bearing Nude Mice Labeled peptides were injected intravenously in a dose of about 56 kBq into F9 (teratocarcinoma)-bearing animals (bodyweight about 25 g). The radioactivity concentration in various organs, and the radioactivity in the excreta was measured using a γ counter at various times after administration of the substance. In addition, the tumour to blood ratio was found at various times on the basis of the concentration of the peptide in tumour and blood.

The biodistribution of Tc-99m-L19-SIP in F9 (teratocarcinoma)-bearing nude mice (mean±SD, n=3) is shown in Table 7.

The tumour to blood ratio of Tc-99m-L19-SIP in F9 (teratocarcinoma)-bearing nude mice (mean±SD, n=3) is shown in Table 8.

Radiolabeled peptides proved to possess favorable properties in animal experiments. For example, Tc-99m-L19-SIP and In-111-MX-DTPA-ε-HN(Lys)-L19-SIP displayed high tumor accumulation of 17.2 (Tc-99m) or 12.9 (In-111) % injected dose per gram (ID/g) at 1 hour post injection (p.i.). Significant tumor retention of 9.4 (Tc-99m) or 13.0 (In-111) % ID/g at 24 hours p.i. was observed. Thus, tumor uptake is significantly higher compared to other known In-111 or Tc-99m labeled antibody fragments (e.g. Kobayashi et al., J. Nuc. Med., Vol. 41(4), pp. 755-762, 2000; Verhaar et al., J. Nuc. Med., Vol. 37(5), pp. 868-872, 1996). The compound's blood clearance lead to tumor/blood ratios of 13:1 and 6:1 respectively, at 24 h p.i.

Most remarkably In-111-MX-DTPA-ε-HN(Lys)-L19-SIP displayed significantly lower kidney uptake and retention (22.5% ID/g) than other highly retained In-111 labeled recombinant antibody fragment (120% ID/g) described e.g. by Kobayashi et al. at 24 h p.i. Kidney retention is a very common problem and usually hampers the use of lanthanide labeled compounds in radiotherapy.

The experimental results demonstrate the excellent potential of the radioimmunoconjugates described herein for diagnostic and therapeutic applications, preferably applied to the patient by parenteral administration.

Discussion

The observation that cytotoxic anticancer drugs localize more efficiently in normal tissues than in tumors (37 Bosslet et al., 1998) prompted a wave of studies investigating the possibility of selective drug delivery to tumors. The effective targeting of tumors, however, has two main requisites: 1) a target in the tumor that is specific, abundant, stable and readily available for ligand molecules coming from the bloodstream, and 2) a ligand molecule with suitable pharmakokinetic properties that is easily diffusible from the bloodstream to the tumor and with a high affinity for the target to ensure its efficient and selective accumulation in the tumor.

Due to its distinctive features the tumor microenvironment is a possible pan-tumoral target. In fact, tumor progression induces (and subsequently needs) significant modifications in tumor micro-environment components, particularly those of the extracellular matrix (ECM). The molecules making up the ECM of solid tumors differ both quantitatively and qualitatively from those of the normal ECM. Moreover, many of these tumor ECM components are shared by all solid tumors, accounting for general properties and functions such as cell invasion (both normal cells into tumor tissues and cancer cells into normal tissues) and angiogenesis. Of the numerous molecules constituting the modified tumor ECM, the present inventors have focused attention on a FN isoform containing the ED-B domain (B-FN).

B-FN is widely expressed in the ECM of all solid tumors thus far tested and is constantly associated with angiogenic processes (22 Castellani et al.; 1994), but is otherwise undetectable in normal adult tissues (17 Carnemolla et al., 1989). Targeted delivery of therapeutic agents to the subendothelial ECM overcomes problems associated with interstitial hypertension of solid tumors (38 Jain et al. 1988; 39 Jain, 1997; 40 Jain R K, 1999).

L19 (13 Pini et al. 1998; 25 Viti, Canc. Res., 23 Tarli, et al., 1999), an scFv with a high affinity (Kd=$5.4 \times 10^{-11}$M) for the ED-B domain of FN, selectively and efficiently accumulates in vivo around tumor neo-vasculature and is able to selectively transport and concentrate in the tumor mass any one of a number of therapeutic molecules to which it is conjugated (28 Birchler et al., 1999; 29 Nilsson, et al., 2001; 30 Halin et al. 2002; 31 Carnemolla et al., 2002). The ability of L19 to selectively target tumors has also been demonstrated in patients using scintigraphic techniques.

The present specification reports on tumor vascular targeting performance and pharmacokinetics of three different L19 human antibody formats: the scFv, the mini-immunoglobulin/small immunoprotein (SIP) and complete human IgG1.

The SIP molecule was obtained by fusion of the scFv(L19) to the εCH4 domain of the secretory isoform $S_2$ of human IgE. The εCH4 is the domain that allows dimerization of IgE molecules and the $S_2$ isoform contains a cysteine at the COOH terminal that covalently stabilizes the dimer through an interchain disulphide bond (35 Batista et al., 1996). The IgE binding sites for FcεRI reside in the CH3 domain (41 Turner and Kinet, 1999; 42 Vangelista et al., 1999; 43 Garman et al., 2000), so scFv fused to εCH4 domain in accordance with embodiments of the present invention does not activate any signalling leading to hypersensitivity reactions.

The performance of these three formats in two different tumor models in mouse has been studied: in murine F9 teratocarcinoma and human SK-MEL-28 melanoma. The first is a rapidly growing tumor that, once implanted, kills the animals in about two weeks. SK-MEL-28 tumor, on the other hand, presents a biphasic growth curve, with an early, fast, growth phase followed by a second, slower, phase. It has previously been shown that the amount of ED-B in F9 teratocarcinoma remains stable during tumor growth (23 Tarli, et al., 1999); by contrast, ED-B accumulates in SK-MEL-28 melanoma proportionally to the ability of the tumor to grow (23 Tarli et al., 1999), with abundant ED-B being found in the first phase and a lesser amount in the second. The use of SK-MEL-28 melanoma tumor allowed long-term biodistribution studies without dramatic variations of tumoral mass (FIG. 2) that could give rise to misinterpretation of results.

Comparative studies of the three L19 antibody formats in terms of stability in vivo showed that L19-SIP and L19-IgG1 maintained, for the duration of experiments (144 h), the same immunoreactivity and molecular mass in plasma as before injection. By contrast, scFv(L19) rapidly lost its immunoreactivity in plasma and generated aggregates that were too large to enter the gel filtration chromatography column. Such aggregation of the scFv is very likely responsible for the ratio between % ID/g of tumor and lung, since aggregates could accumulate in the microvasculature of the lung (Table 3). For all three formats, the blood clearance is mediated mainly via the kidney, showing a biphasic curve with an α and a β phase, reported in Table 4, which is inversely proportional to molecular size.

The accumulation of the different antibody formats in the tumors studied was a consequence of the clearance rate and in vivo stability of the molecules. Using the scFv, the maximum percent injected dose per gram (% ID/g) was observed 3 h after injection of the radiolabeled antibody and then rapidly decreased. Using the SIP, the % ID/g in tumors was 2-5 times higher than that of the scFv, reaching a maximum 4-6 hours after injection. This pattern was observed in both F9 and SK-MEL-28 tumors. By contrast, the accumulation of IgG1 in tumors rose constantly during the experiments. However, due to its slow clearance, the tumor-blood ratio of the % ID/g after 144 hours was only about 3, compared to a ratio of 10 for the scFv and 70 for the SIP after the same period of time (FIG. 4).

The same distinctive properties of in vivo stability, clearance and tumor targeting performance shown by the three antibody formats studied here may be exploited for different diagnostic and/or therapeutic purposes, depending on the clinical needs and disease. For instance, radiolabeled antibodies showing good tumor-organ and tumor-blood ratios soon after injection are necessary for in vivo diagnostic immunoscintigraphy, mainly because short half-life isotopes are used in such analysis.

Different approaches are possible using antibody as a vehicle for therapeutic agents: delivery of substances that display their therapeutic effects after reaching their targets (e.g., photosensitisers activated only on the targets), for which the absolute amount delivered to the tumor is relevant; delivery of substances that exert their therapeutic and toxic effects even before reaching the target (e.g., the p-emitter Yttrium-90), for which particular attention must be given to the ratio of the area under the curves of tumor and blood accumulation as a function of time, in order to minimize the systemic toxicity and to maximize the anti-tumor therapeutic effect.

L19-SIP, for instance, seems to offer the best compromise of molecular stability, clearance rate and tumor accumulation. Similar fusion proteins composed of scFv antibody fragments bound to a dimerizing domain have already been described (44 Hu et al, 1996; 33 Li et al., 1997), but in both cases the human γ1CH3 was used as the dimerizing domain. The usage of the human $\epsilon_{S2}$CH4 domain provides an easy way of getting a covalent stabilization of the dimer. In addition, the disulphide bridge formed by the C-terminal cysteine residues can be easily reduced in mild enough conditions to preserve the overall structure of the molecule, thus providing a readily accessible reactive group for radiolabelling or chemical conjugation. This feature seems particularly promising in the view of the clinical potential.

L19-IgG1 gathers abundantly in tumors, and even though this accumulation is offset by a slow blood clearance rate, the three step procedure to remove circulating antibodies may be used to allow its use not only for therapeutic purposes but also for diagnostic immunoscintigraphy (45 Magnani et al. 2000).

REFERENCES

1. Shawler et al. J. Immunol., 135: 1530-1535, 1985
2. Miller et al. Blood, 62: 988-995, 1983.
3. Hakimi et al. J. Immunol., 147: 1352-1359, 1991.
4. Stephens et al. Immunology, 85: 668-674, 1995.
5. Riechmann et al. Nature, 332: 323-327, 1988.
6. Junghans et al. Cancer Res., 50: 1495-1502, 1990.
7. McCafferty et al. Nature, 348: 552-554, 1990.

8. Lowman et al. Biochemistry, 30: 10832-10838, 1991
9. Nilsonn et al. Advanced Drug Delivery Reviews, 43: 165-196, 2000.
10. Winter et al. Annu. Rev. Immunol., 12: 433-455, 1994.
11. Reichert. Nature Biotech., 19: 819-822, 2001.
12. Huls et al. Nature Biotech., 17: 276-281, 1999,
13. Pini et al. J Biol Chem, 273: 21769-21776, 1998.
14. Neri and Zardi. Advanced Drug Delivery Reviews, 31: 43-52, 1998.
15. Bissel and Radisky. Nature Reviews—Cancer., 1: 46-54, 2001
16. Balza et al. *FEBS Lett.*, 228: 42-44, 1988
17. Carnemolla et al. J. Cell. Biol., 108: 1139-1148, 1989
18. Borsi et al. *FEBS Lett.*, 261: 175-178, 1990
19. Borsi et al. J. Biol. Chem., 270: 6243-6245, 1995.
20. Zardi et al. *EMBO J.*, 6: 2337-2342, 1987.
21. ffrench-Constant et al. J. Cell Biol., 109: 903-914, 1989.
22. Castellani et al. Int J Cancer, 59: 612-618, 1994
23. Tarli et al. Blood, 94:192-198, 1999.
24. Carnemolla et al. Int J Cancer, 68: 397-405, 1996.
25. Viti et al. Cancer Res, 59: 347-353, 1999.
26. Neri et al. Nature Biotechnol, 15: 1271-1275, 1997.
27. Demartis et al. Eur J Nucl Med, 28: 4534-4539, 2001.
28. Birchler et al. Nat Biotechnol, 17: 984-988, 1999
29. Nilsson et al. Cancer Res., 61: 711-716, 2001.
30. Halin et al. Nature Biotechnol. In the press, 2002.
31. Carnemolla et al. Blood, 99: 2002
32. Wu et al. Proc. Nat. Acad. Sci. U.S.A., 97: 8495-8500, 2000.
33. Li et al. Protein Engineering, 10: 731-736, 1997
34. Pini et al. J. Immunol. Methods, 206: 171-183, 1997.
35. Batista et al. J. Exp. Med., 184: 2197-205, 1996.
36. Riske et al. J. Biol. Chem., 266: 11245-11251, 1991'.
37. Bosslet et al. Cancer Res., 58:1195-1201, 1998.
38. Jain and Baxter. Cancer Res., 48: 7022-7032, 1988.
39. Jain. Vascular and interstitial physiology of tumors. Role in cancer detection and treatment. In: R. Bicknell, C. E. Lewis and N. Ferrara (eds). Tumour Angiogenesis, pp. 45-59. New York: Oxford University Press, 1997.
40. Jain. Annu. Rev. Biomed. Eng., 1: 241-263, 1999.
41. Turner and Kinet. Nature, 402 Suppl., B24-B30, 1999.
42. Vangelista et al. Jour. Clin. Invest., 103:1571-1578, 1999.
43. Garman et al. Nature, 406: 259-266, 2000.
44. Hu et al. Cancer Res., 56: 3055-3061, 1996.
45. Magnani et al. Br. J. Cancer, 82: 616-620, 2000.

TABLE 1

Immunoreactivity (I*) and radioactivity recovery (R) from Superdex 200 of the radiolabeled antibodies, at different times after i.v. injection

| | Time(h) | | | | | | | | | | |
|---|---|---|---|---|---|---|---|---|---|---|---|
| | 3 | | 6 | | 24 | | 48 | | 72 | | 144 | |
| | I | R | I | R | I | R | I | R | I | R | I | R |
| L19(scFv) | 36 | 54 | 32 | 58 | 27 | nd | 14 | nd | 9 | nd | 4 | nd |
| L19SIP | 100 | 100 | 100 | 96 | 100 | 94 | 95 | 96 | 100 | nd | 95 | nd |
| L19IgG1 | 100 | 100 | 100 | 100 | 95 | 100 | 100 | 100 | 100 | 100 | 95 | 100 |

Immunoreactivity (%) and radioactivity recovery (%) from Superdex 200 were determined in plasma as described in Materials and Methods.
*To normalize, the results of the Immunoreactivity test are referred to the percentage values of the Immunoreactivity before I.v. Injection.
nd: not determined TABLE 2a Biodistribution experiments of radiolabeled L19 and D1.3 antibody fragments in SK-MEL-28 tumor-bearing mice

| | 3 h | 6 h | 24 h | 48 h | 72 h | 144 h |
|---|---|---|---|---|---|---|
| L19(scFv) | | | | | | |
| TUMOR | 2.47 ± 0.65 | 2.01 ± 0.72 | 1.62 ± 0.43 | 0.95 ± 0.14 | 0.68 ± 0.04 | 0.32 ± 0.14 |
| Blood | 1.45 ± 0.58 | 0.54 ± 0.12 | 0.10 ± 0.03 | 0.04 ± 0.01 | 0.03 ± 0.02 | 0.03 ± 0.01 |
| Liver | 0.48 ± 0.20 | 0.18 ± 0.05 | 0.04 ± 0.01 | 0.02 ± 0.00 | 0.02 ± 0.01 | 0.02 ± 0.00 |
| Spleen | 0.67 ± 0.28 | 0.27 ± 0.04 | 0.07 ± 0.02 | 0.03 ± 0.00 | 0.02 ± 0.01 | 0.02 ± 0.00 |
| Kidney | 4.36 ± 0.32 | 1.67 ± 0.08 | 0.16 ± 0.01 | 0.06 ± 0.01 | 0.04 ± 0.02 | 0.03 ± 0.00 |
| Intestine | 0.77 ± 0.21 | 0.57 ± 0.05 | 0.24 ± 0.06 | 0.17 ± 0.04 | 0.12 ± 0.05 | 0.09 ± 0.01 |
| Heart | 0.77 ± 0.20 | 0.31 ± 0.07 | 0.07 ± 0.02 | 0.02 ± 0.00 | 0.02 ± 0.01 | 0.02 ± 0.00 |
| Lung | 2.86 ± 0.34 | 1.50 ± 0.67 | 1.07 ± 0.42 | 0.73 ± 0.39 | 0.55 ± 0.11 | 0.51 ± 0.22 |
| D1.3(scFv) | | | | | | |
| TUMOR | 1.03 ± 0.74 | 0.87 ± 0.42 | 0.15 ± 0.10 | 0.07 ± 0.02 | nd | nd |
| Blood | 1.52 ± 0.86 | 0.81 ± 0.13 | 0.02 ± 0.00 | 0.01 ± 0.00 | nd | nd |
| Liver | 1.19 ± 0.65 | 0.66 ± 0.26 | 0.14 ± 0.04 | 0.03 ± 0.08 | nd | nd |
| Spleen | 1.05 ± 0.88 | 0.42 ± 0.33 | 0.07 ± 0.02 | 0.05 ± 0.01 | nd | nd |
| Kidney | 3.01 ± 2.48 | 1.03 ± 0.76 | 0.48 ± 0.01 | 0.18 ± 0.05 | nd | nd |
| Intestine | 0.56 ± 0.54 | 0.56 ± 0.13 | 0.17 ± 0.03 | 0.02 ± 0.01 | nd | nd |
| Heart | 0.86 ± 0.54 | 0.55 ± 0.84 | 0.02 ± 0.01 | 0.01 ± 0.00 | nd | nd |
| Lung | 1.28 ± 0.65 | 1.06 ± 0.88 | 0.04 ± 0.01 | 0.03 ± 0.01 | nd | nd |

The results are expressed as percent of antibody injected dose per gram of tissue (% ID/g) ± SD
nd: not determined TABLE 2b Biodistribution experiments of radiolabeled L19-SIP and D1.3-SIP in SK-MEL-28 tumor-bearing mice

|  | 3 h | 6 h | 24 h | 48 h | 72 h | 144 h |
|---|---|---|---|---|---|---|
| L19SIP | | | | | | |
| TUMOR | 5.23 ± 0.65 | 6.14 ± 2.23 | 4.20 ± 2.47 | 2.57 ± 0.31 | 2.33 ± 0.90 | 1.49 ± 0.65 |
| Blood | 9.82 ± 0.68 | 5.03 ± 0.52 | 1.39 ± 0.06 | 0.29 ± 0.04 | 0.08 ± 0.02 | 0.02 ± 0.01 |
| Liver | 2.65 ± 0.14 | 1.74 ± 0.31 | 0.50 ± 0.04 | 0.19 ± 0.01 | 0.10 ± 0.02 | 0.05 ± 0.01 |
| Spleen | 3.76 ± 0.36 | 2.43 ± 0.24 | 0.71 ± 0.05 | 0.26 ± 0.04 | 0.13 ± 0.01 | 0.17 ± 0.18 |
| Kidney | 7.33 ± 0.91 | 3.87 ± 0.21 | 1.09 ± 0.05 | 0.30 ± 0.04 | 0.14 ± 0.02 | 0.05 ± 0.01 |
| Intestine | 1.45 ± 0.24 | 1.44 ± 0.29 | 1.06 ± 0.43 | 0.56 ± 0.08 | 0.40 ± 0.02 | 0.18 ± 0.00 |
| Heart | 4.16 ± 0.30 | 2.15 ± 0.08 | 0.52 ± 0.05 | 0.13 ± 0.03 | 0.06 ± 0.01 | 0.02 ± 0.01 |
| Lung | 7.72 ± 0.60 | 5.41 ± 0.55 | 1.81 ± 0.40 | 0.59 ± 0.29 | 0.19 ± 0.03 | 0.05 ± 0.01 |
| D1.3SIP | | | | | | |
| TUMOR | 3.80 ± 0.30 | 1.65 ± 0.12 | 0.70 ± 0.00 | 0.26 ± 0.01 | 0.07 ± 0.01 | 0.04 ± 0.03 |
| Blood | 10.40 ± 0.81 | 4.45 ± 0.14 | 1.21 ± 0.01 | 0.32 ± 0.00 | 0.08 ± 0.01 | 0.06 ± 0.02 |
| Liver | 4.05 ± 0.98 | 2.73 ± 0.33 | 1.43 ± 0.07 | 0.51 ± 0.21 | 0.15 ± 0.08 | 0.02 ± 0.01 |
| Spleen | 3.31 ± 0.66 | 1.76 ± 0.50 | 0.82 ± 0.12 | 0.46 ± 0.20 | 0.15 ± 0.05 | 0.04 ± 0.02 |
| Kidney | 8.41 ± 0.49 | 4.64 ± 0.06 | 1.47 ± 0.05 | 0.36 ± 0.03 | 0.16 ± 0.03 | 0.06 ± 0.01 |
| Intestine | 2.03 ± 0.55 | 1.06 ± 0.20 | 1.02 ± 0.06 | 0.14 ± 0.03 | 0.08 ± 0.02 | 0.12 ± 0.04 |
| Heart | 3.28 ± 0.20 | 1.81 ± 0.02 | 0.29 ± 0.01 | 0.06 ± 0.00 | 0.05 ± 0.01 | 0.04 ± 0.01 |
| Lung | 6.16 ± 0.28 | 4.52 ± 0.07 | 1.16 ± 0.05 | 0.09 ± 0.00 | 0.06 ± 0.01 | 0.05 ± 0.01 |

The results are expressed as percent of antibody injected dose per gram of tissue (% ID/g) ± SD
nd: not determined TABLE 2c Biodistribution experiments of radiolabeled L19IgG1 and hIgG1k in SK-MEL-28 tumor-bearing mice

|  | 3 h | 6 h | 24 h | 48 h | 72 h | 144 h |
|---|---|---|---|---|---|---|
| L19IgG1 | | | | | | |
| TUMOR | 4.46 ± 0.08 | 5.39 ± 1.01 | 6.70 ± 2.10 | 7.80 ± 2.51 | 8.90 ± 2.52 | 11.22 ± 3.19 |
| Blood | 16.04 ± 0.81 | 12.02 ± 1.65 | 8.31 ± 1.77 | 5.12 ± 1.42 | 5.02 ± 3.81 | 4.87 ± 0.26 |
| Liver | 4.03 ± 0.37 | 6.77 ± 0.53 | 2.41 ± 0.35 | 1.45 ± 0.41 | 1.26 ± 0.71 | 1.09 ± 0.16 |
| Spleen | 4.63 ± 1.34 | 6.37 ± 1.37 | 2.51 ± 0.47 | 2.01 ± 0.32 | 1.80 ± 1.02 | 1.51 ± 0.29 |
| Kidney | 4.47 ± 0.39 | 5.12 ± 0.47 | 3.07 ± 0.35 | 1.73 ± 0.63 | 1.54 ± 1.14 | 1.12 ± 0.44 |
| Intestine | 1.60 ± 0.39 | 1.35 ± 0.65 | 1.43 ± 0.19 | 1.13 ± 0.32 | 1.13 ± 0.98 | 0.97 ± 0.47 |
| Heart | 5.63 ± 0.67 | 4.77 ± 0.52 | 2.87 ± 0.45 | 1.48 ± 0.51 | 1.32 ± 1.09 | 0.92 ± 0.37 |
| Lung | 4.55 ± 0.65 | 5.15 ± 0.62 | 4.16 ± 0.66 | 2.28 ± 0.80 | 1.98 ± 1.60 | 1.42 ± 0.45 |
| hIgG1k | | | | | | |
| TUMOR | nd | 3.28 ± 0.38 | 4.00 ± 0.22 | 2.78 ± 0.20 | nd | 2.32 ± 0.26 |
| Blood | nd | 10.12 ± 0.35 | 7.87 ± 0.25 | 6.24 ± 0.34 | nd | 5.41 ± 0.51 |
| Liver | nd | 4.02 ± 0.09 | 2.06 ± 0.10 | 1.90 ± 0.24 | nd | 1.28 ± 0.03 |
| Spleen | nd | 4.47 ± 0.28 | 1.82 ± 0.01 | 1.42 ± 0.19 | nd | 1.24 ± 0.03 |
| Kidney | nd | 5.40 ± 0.19 | 2.56 ± 0.06 | 2.08 ± 0.22 | nd | 1.30 ± 0.15 |
| Intestine | nd | 0.72 ± 0.07 | 0.46 ± 0.05 | 0.36 ± 0.03 | nd | 0.31 ± 0.01 |
| Heart | nd | 3.80 ± 0.15 | 2.52 ± 0.21 | 0.99 ± 0.18 | nd | 1.48 ± 0.13 |
| Lung | nd | 4.82 ± 0.92 | 3.64 ± 0.08 | 1.75 ± 0.32 | nd | 1.09 ± 0.13 |

The results are expressed as percent of antibody injected dose per gram of tissue (% ID/g) ± SD
nd: not determined

TABLE 3

Tumor-organ ratios of the % ID/g of the radiolabeled L19 antibody formats in SK-MEL-28 tumor-bearing mice.

| | L19(ScFv) | | | | | | L19SIP | | | | | | L19IgG1 | | | | | |
|---|---|---|---|---|---|---|---|---|---|---|---|---|---|---|---|---|---|---|
| Time(h) | 3 | 6 | 24 | 48 | 72 | 144 | 3 | 6 | 24 | 48 | 72 | 144 | 3 | 6 | 24 | 48 | 72 | 144 |
| TUMOR | 1 | 1 | 1 | 1 | 1 | 1 | 1 | 1 | 1 | 1 | 1 | 1 | 1 | 1 | 1 | 1 | 1 | 1 |
| Blood | 1.7 | 3.7 | 16.2 | 23.7 | 22.7 | 10.7 | 0.5 | 1.2 | 3.0 | 8.9 | 29.1 | 74.5 | 0.3 | 0.4 | 0.8 | 1.5 | 1.8 | 2.3 |
| Liver | 5.1 | 11.1 | 40.5 | 47.5 | 34.0 | 16.0 | 2.0 | 3.5 | 8.4 | 13.5 | 23.3 | 29.8 | 0.7 | 0.8 | 2.8 | 5.4 | 7.1 | 6.3 |
| Spleen | 3.7 | 7.4 | 23.1 | 31.6 | 34.0 | 16.0 | 1.4 | 2.5 | 5.9 | 10.0 | 17.9 | 8.8 | 0.7 | 0.6 | 2.7 | 3.9 | 4.9 | 7.4 |

TABLE 3-continued

Tumor-organ ratios of the % ID/g of the radiolabeled L19
antibody formats in SK-MEL-28 tumor-bearing mice.

| | L19(ScFv) | | | | | | L19SIP | | | | | | L19IgG1 | | | | | |
|---|---|---|---|---|---|---|---|---|---|---|---|---|---|---|---|---|---|---|
| Time(h) | 3 | 6 | 24 | 48 | 72 | 144 | 3 | 6 | 24 | 48 | 72 | 144 | 3 | 6 | 24 | 48 | 72 | 144 |
| Kidney | 0.6 | 1.2 | 10.1 | 15.8 | 17.0 | 10.7 | 0.7 | 1.6 | 3.8 | 8.6 | 16.6 | 29.8 | 0.7 | 1.0 | 2.2 | 4.5 | 5.8 | 5.3 |
| Intestine | 3.2 | 3.5 | 6.7 | 5.6 | 5.7 | 3.6 | 3.6 | 4.3 | 4.0 | 4.6 | 5.8 | 8.3 | 2.8 | 4.0 | 4.7 | 6.9 | 7.9 | 7.1 |
| Heart | 3.2 | 6.5 | 23.1 | 47.5 | 34.0 | 16.0 | 1.3 | 2.9 | 8.1 | 20.0 | 38.8 | 74.5 | 0.8 | 1.1 | 2.3 | 5.3 | 6.7 | 5.8 |
| Lung | 0.9 | 1.3 | 1.5 | 1.3 | 1.2 | 0.6 | 0.7 | 1.1 | 2.3 | 4.3 | 12.3 | 29.8 | 0.7 | 1.0 | 1.6 | 3.4 | 4.5 | 3.7 |

TABLE 4

Kinetic parameters for blood clearance
of the three L19 antibody formats

| | α | | β | |
|---|---|---|---|---|
| | (%)[a] | t½[h] | (%)[a] | t½[h] |
| L19(scFv) | 96.7 | 0.53 | 3.3 | 8.00 |
| L19-SIP | 83.7 | 1.06 | 16.3 | 10.66 |
| L19-IgG1 | 76.9 | 1.48 | 23.1 | 106.7 |

[a] Relative magnitude of the two half-life components

TABLE 5

Biodistribution experiments of radiolabeled
L19(scFv) and L19SIP in F9 tumor-bearing mice

| | 3 h | 6 h | 24 h | 48 h |
|---|---|---|---|---|
| L19(scFv) | | | | |
| TUMOR | 10.46 ± 1.75 | 8.15 ± 2.63 | 3.18 ± 0.83 | 2.83 ± 0.71 |
| Blood | 2.05 ± 0.38 | 1.88 ± 1.14 | 0.17 ± 0.01 | 0.06 ± 0.02 |
| Liver | 1.62 ± 1.67 | 0.73 ± 0.51 | 0.07 ± 0.01 | 0.04 ± 0.02 |
| Spleen | 1.53 ± 0.36 | 0.90 ± 0.54 | 0.11 ± 0.01 | 0.05 ± 0.01 |
| Kidney | 12.70 ± 0.73 | 4.37 ± 0.98 | 0.24 ± 0.03 | 0.18 ± 0.08 |
| Intestine | 0.68 ± 0.15 | 0.95 ± 0.23 | 0.24 ± 0.01 | 0.17 ± 0.06 |
| Heart | 1.35 ± 0.21 | 0.81 ± 0.38 | 0.08 ± 0.02 | 0.04 ± 0.01 |
| Lung | 2.88 ± 0.29 | 2.06 ± 0.69 | 0.38 ± 0.60 | 0.33 ± 0.05 |
| L19SIP | | | | |
| TUMOR | 17.46 ± 1.93 | 16.65 ± 2.59 | 15.32 ± 2.17 | 12.00 ± 1.91 |
| Blood | 13.51 ± 0.57 | 9.62 ± 1.18 | 1.73 ± 0.02 | 1.14 ± 0.20 |
| Liver | 2.81 ± 0.37 | 2.39 ± 0.13 | 0.54 ± 0.14 | 0.32 ± 0.00 |
| Spleen | 3.42 ± 0.26 | 2.66 ± 0.27 | 0.61 ± 0.09 | 0.37 ± 0.01 |
| Kidney | 9.18 ± 0.76 | 5.85 ± 0.50 | 1.16 ± 0.05 | 0.76 ± 0.06 |
| Intestine | 0.95 ± 0.03 | 1.36 ± 0.21 | 0.83 ± 0.11 | 1.04 ± 0.14 |
| Heart | 4.64 ± 0.24 | 3.67 ± 0.46 | 0.67 ± 0.06 | 0.46 ± 0.07 |
| Lung | 5.61 ± 0.01 | 5.93 ± 0.57 | 1.66 ± 0.19 | 0.91 ± 0.08 |

The results are expressed as percent of antibody injected dose per gram of tissue (% ID/g) ± SD
nd: not determined

TABLE 6

| | % of dose/g of tissue | | |
|---|---|---|---|
| | 1 h p.i. | 3 h p.i. | 24 h p.i. |
| Spleen | 5.05 ± 1.04 | 4.27 ± 0.27 | 4.86 ± 1.77 |
| Liver | 10.80 ± 1.52 | 10.57 ± 1.44 | 10.68 ± 1.51 |
| Kidney | 14.30 ± 1.45 | 16.71 ± 2.42 | 22.48 ± 6.79 |
| Lung | 9.94 ± 1.72 | 6.15 ± 0.80 | 3.03 ± 0.95 |
| Stomach without contents | 1.10 ± 0.13 | 1.62 ± 0.19 | 1.66 ± 0.24 |
| Intestine with contents | 1.67 ± 0.14 | 2.65 ± 0.30 | 2.64 ± 1.40 |
| Tumor | 12.93 ± 2.76 | 10.18 ± 2.28 | 12.96 ± 3.13 |
| Blood | 17.10 ± 1.49 | 9.08 ± 0.96 | 1.98 ± 0.47 |

TABLE 7

| | % of dose/g of tissue | | |
|---|---|---|---|
| | 1 h p.i. | 3 h p.i. | 24 h p.i. |
| Spleen | 6.92 ± 1.3 | 5.37 ± 0.23 | 2.06 ± 0.48 |
| Liver | 14.65 ± 0.81 | 12.43 ± 0.37 | 4.62 ± 0.52 |
| Kidney | 22.07 ± 1.87 | 15.99 ± 1.10 | 5.92 ± 1.18 |
| Lung | 10.06 ± 1.67 | 5.33 ± 0.49 | 1.32 ± 0.25 |
| Stomach without contents | 2.18 ± 0.39 | 2.12 ± 0.09 | 1.15 ± 0.08 |
| Intestine with contents | 3.03 ± 0.25 | 3.62 ± 0.58 | 1.20 ± 0.12 |
| Tumour | 17.20 ± 7.49 | 18.79 ± 5.35 | 9.42 ± 3.84 |
| Blood | 16.53 ± 2.04 | 7.42 ± 0.21 | 0.73 ± 0.14 |

TABLE 8

| | 1 h p.i. | 3 h p.i. | 24 h p.i. |
|---|---|---|---|
| Tumour to blood ratio | 1.01 ± 0.33 | 2.54 ± 0.74 | 12.81 ± 4.03 |

LIST OF SEQUENCES

SEQ ID NO. 1
S F S M S
SEQ ID NO. 2
S I S G S S G T T Y Y A D S V K G
SEQ ID NO. 3
P F P Y F D Y
SEQ ID NO. 4
R A S Q S V S S S F L A
SEQ ID NO. 5
Y A S S R A T
SEQ ID NO. 6
Q Q T G R I P P T
SEQ ID NO. 7
G G S G
SEQ ID NO. 8
gtgtgcactcggaggtgcagctgttggagtctggg
SEQ ID NO. 9
gcctccggatttgatttccaccttggtcccttggcc
SEQ ID NO. 10
ctcgtgcactcgcaggtgcagctgcaggagtca
SEQ ID NO. 11
ctctccggacctttgatctcgcgcttggt
SEQ ID NO. 12
tggtgtgcactcggaaattgtgttgacgcagtc
SEQ ID NO. 13
ctctcgtacgtttgatttccaccttggtcc

The invention claimed is:

1. A specific binding member that binds human extra-domain B of fibronectin (ED-B) and comprising
an antigen-binding site that comprises
an antibody heavy chain variable region (VH domain) of an L19 antibody comprising the VH CDR1 sequence set forth in SEQ ID NO: 1, the VH CDR2 sequence set forth in SEQ ID NO: 2 and the VH CDR3 sequence set forth in SEQ ID NO: 3,
an antibody light chain variable region (VL domain) of an L19 antibody comprising the VL CDR1 sequence set forth in SEQ ID NO: 4, the VL CDR2 sequence set forth in SEQ ID NO: 5 and the VL CDR3 sequence set forth in SEQ ID NO: 6; and
a εS2-CH4 domain,
wherein, said specific binding member exhibits greater accumulation in a tumor expressing said ED-B after 48 hours of administration compared to that achieved by a specific binding member comprising said VH and VL domains but lacking said εS2-CH4 domain.

2. A specific binding member according to claim 1 which competes with said L19 antibody comprising said antibody VH domain comprising said SEQ ID NOs: 1-3 and said antibody VL domain comprising said SEQ ID NOs: 4-6 for binding to ED-B.

3. A specific binding member according to claim 1 wherein the antibody VH domain and antibody VL domain are within an scFv antibody molecule that is fused to said εS2-CH4 domain.

4. A specific binding member according to claim 3 wherein the scFv antibody molecule is fused to said εS2-CH4 domain via a linker peptide.

5. A specific binding member according to claim 4 wherein the linker peptide comprises the polypeptide sequence set forth in SEQ ID NO: 7 (GGSG).

6. A specific binding member according to claim 1 which comprises an scFV, a mini-immunoglobulin or a whole IgG1 antibody molecule.

7. A specific binding member according to claim 1 which is conjugated to a radioisotope.

8. A specific binding member according to claim 7 wherein the radioisotope is a radioisotope of Tc, Re, In, Y or Lu.

9. A specific binding member according to claim 7 wherein the radioisotope is 94mTc, 99mTc, 186Re, 203Pb 67Ga, 68Ga, 43Sc, 47Sc, 110mIn, 111In, 97Ru, 62Cu, 64Cu, 67Cu, 68Cu, 86Y, 88Y, 90Y, 121Sn, 161Tb, 53Sm, 166Ho, 105Rh, 177Lu, 172Lu or 18F.

10. The specific binding member according to claim 1 which is in monomeric or dimeric form.

11. A composition comprising a specific binding member according to claim 1 and a pharmaceutically acceptable excipient, carrier, buffer or stabilizer.

12. A composition according to claim 11, which is suitable for oral or intravenous administration.

13. A composition according to claim 11 which is a diagnostic composition or a therapeutic composition.

\* \* \* \* \*

SEQUENCE LISTING

<160> NUMBER OF SEQ ID NOS: 13

<210> SEQ ID NO 1
<211> LENGTH: 5
<212> TYPE: PRT
<213> ORGANISM: Homo sapiens

<400> SEQUENCE: 1

Ser Phe Ser Met Ser
1               5

<210> SEQ ID NO 2
<211> LENGTH: 17
<212> TYPE: PRT
<213> ORGANISM: Homo sapiens

<400> SEQUENCE: 2

Ser Ile Ser Gly Ser Ser Gly Thr Thr Tyr Tyr Ala Asp Ser Val Lys
1               5                   10                  15

Gly

<210> SEQ ID NO 3
<211> LENGTH: 7
<212> TYPE: PRT
<213> ORGANISM: Homo sapiens

<400> SEQUENCE: 3

Pro Phe Pro Tyr Phe Asp Tyr
1               5

<210> SEQ ID NO 4
<211> LENGTH: 12
<212> TYPE: PRT
<213> ORGANISM: Homo sapiens

<400> SEQUENCE: 4

Arg Ala Ser Gln Ser Val Ser Ser Ser Phe Leu Ala
1               5                   10

<210> SEQ ID NO 5
<211> LENGTH: 7
<212> TYPE: PRT
<213> ORGANISM: Homo sapiens

<400> SEQUENCE: 5

Tyr Ala Ser Ser Arg Ala Thr
1               5

<210> SEQ ID NO 6
<211> LENGTH: 9
<212> TYPE: PRT
<213> ORGANISM: Homo sapiens

<400> SEQUENCE: 6

Gln Gln Thr Gly Arg Ile Pro Pro Thr
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 7

Gly Gly Ser Gly
1

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgtgcactc ggaggtgcag ctgttggagt ctggg                          35

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcctccggat ttgatttcca ccttggtccc ttggcc                         36

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcgtgcact cgcaggtgca gctgcaggag tca                            33

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctctccggac cgtttgatct cgcgcttggt                                30

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggtgtgcac tcggaaattg tgttgacgca gtc                            33

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 13
ctctcgtacg tttgatttcc accttggtcc                                          30
```